(12) United States Patent
Hashimoto et al.

(10) Patent No.: US 6,754,600 B2
(45) Date of Patent: Jun. 22, 2004

(54) DEVICE FOR EVALUATING INTERNAL QUALITY OF VEGETABLE OR FRUIT, METHOD FOR WARM-UP OPERATION OF THE DEVICE, AND METHOD FOR MEASURING INTERNAL QUALITY

(75) Inventors: Hirotsugu Hashimoto, Saitama (JP); Norio Taniguchi, Saitama (JP); Motoshi Tanaka, Saitama (JP); Yoshihide Nishiyama, Saitama (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 0 days.

(21) Appl. No.: 10/009,593

(22) PCT Filed: Apr. 13, 2001

(86) PCT No.: PCT/JP01/03196

§ 371 (c)(1),
(2), (4) Date: Dec. 11, 2001

(87) PCT Pub. No.: WO01/79814

PCT Pub. Date: Oct. 25, 2001

(65) Prior Publication Data

US 2002/0161540 A1 Oct. 31, 2002

(51) Int. Cl.[7] ............................................. G01N 37/00
(52) U.S. Cl. ..................... 702/81; 356/432; 356/433; 356/434; 356/436; 356/446; 250/339.01; 250/339.07; 250/341.1; 250/339.1; 250/339.12
(58) Field of Search .......................... 702/81; 356/432, 356/433, 434, 436, 440; 250/339.01, 339.07, 341.1, 339.1, 339.12

(56) References Cited

U.S. PATENT DOCUMENTS 3,930,994 A * 1/1976 Conway et al. ............. 209/579
5,084,807 A * 1/1992 McKechnie et al. ........ 362/228
5,844,678 A * 12/1998 Ito et al. ..................... 356/244
6,137,581 A * 10/2000 Kimura et al. .............. 356/433
6,233,051 B1 * 5/2001 Kimura et al. .............. 356/433
6,334,092 B1 * 12/2001 Hashimoto et al. ........... 702/81
6,359,918 B1 * 3/2002 Bielas ..................... 372/38.01
6,512,577 B1 * 1/2003 Ozanich ...................... 356/73
6,563,579 B1 * 5/2003 Kimura et al. .............. 356/246

* cited by examiner

Primary Examiner—John Barlow
Assistant Examiner—Anthony T. Dougherty
(74) Attorney, Agent, or Firm—Sughrue Mion, PLLC

(57) ABSTRACT

An extremely convenient apparatus for evaluating the inner quality of vegetables and fruits which is small and inexpensive, can be introduced easily even by small-scaled enterprisers, in which an installation place can be changed easily, and safety and promptness of the replacing work of light sources are fully taking into consideration is provided. An apparatus for evaluating the inner quality of vegetables and fruits 1 comprising: a place bed 3 on which vegetables and fruits A are placed; light sources 4, 4 disposed to irradiate vegetables and fruits A; a spectra/detection unit 28 for making spectra in transmission light C having transmitted through vegetables and fruits A to detect the optical strength; an operation processing section 31 for calculating and evaluating the quality evaluation amount of the sugar degree and the ripening degree on the basis of the detection signal; and a display panel 36 for displaying the quality evaluation amount of the sugar degree and the ripening degree, the apparatus capable of being installed on the table, and also being portable. Further, a light source peripheral temperature $T_1$ and an environmental temperature $T_2$ are detected in a manner of a lapse of time, the light source peripheral temperature $T_1$ is compared with a safety setting temperature $T_w$ or the environmental temperature $T_2$, and the fact that the light source temperature is fully lowered is reported.

22 Claims, 34 Drawing Sheets

| Optical strength | $P_1$ | $P_2$ | | | | | | | $P_9$ | $P_{10}$ |
|---|---|---|---|---|---|---|---|---|---|---|
| Measurement time | $T_1$ | $T_2$ | | | | | | | $T_9$ | $T_{10}$ |

FIG.35

DEVICE FOR EVALUATING INTERNAL QUALITY OF VEGETABLE OR FRUIT, METHOD FOR WARM-UP OPERATION OF THE DEVICE, AND METHOD FOR MEASURING INTERNAL QUALITY

This application claims benefit of 35 U.S.C. 371 of PCT/JP01/03196 filed on Apr. 13, 2000 and 35 U.S.C. 119 of Japanese Application No. 2000-111524 filed on Apr. 13, 2000, Japanese Application No. 2000-232086 filed on Jul. 31, 2000, Japanese Application No. 2000-232085 filed on Jul. 31, 2000, Japanese Application No. 2000-260042 filed on Aug. 30, 2000, Japanese Application No. 2000-303886 filed on Oct. 3, 2000, and Japanese Application No. 2000-320236 filed on Oct. 20, 2000.

TECHNICAL FIELD

The present invention relates to an apparatus for evaluating the inner quality of vegetables and fruits for measuring the quality evaluation amount of the sugar degree, the ripening degree or the like of vegetables and fruits nondestructively to evaluate the inner quality, a method for warming-up operating and a method for measuring the inner quality in the apparatus.

BACKGROUND ART

There has been heretofore known a method of measuring the inner quality of vegetables and fruits nondestructively to evaluate by irradiating light from a light source on vegetables and fruits and applying spectral analysis to the reflecting light or transmission light.

As the apparatus to which the above method is applied, there has been known an apparatus installed on the floor of an inspection room or the like and placing vegetables and fruits on the place bed to measure and evaluate them (see Japanese Patent Laid-Open No. Hei 11-125593 Publication, etc.), or an apparatus installed on the selective line or the like and placing vegetables and fruits on the carrying conveyor to measure and evaluate them (see Japanese Patent Laid-Open No. Hei 11-337480 Publication, etc.).

However, the above-described conventional apparatuses are large in type and expensive, and small-scaled enterprisers were very hard to introduce them in terms of installation places, purchase expenses and so on. Further, when the apparatuses are once installed, their installation place cannot be changed easily, thus being inconvenient.

Further, in the apparatus placing vegetables and fruits on the place bed to measure and evaluate them, a cover for shielding disturbance light is disposed, and when the cover is closed, automatic measurement is carried out. It is, however, troublesome to close the cover separately, and it takes much time for measurement.

Further, a halogen lamp or the like as a light source has its service life, and if an over-current should flow, it would possibly be broken. In such a case, the lamp has to be replaced, but in the conventional apparatuses, the safety and the promptness in replacing work have not at all been taken into consideration.

Moreover, in such apparatuses as described, it requires a fixed time till the spectrum of a light source is stabilized after a power switch has been turned on. Unless the spectrum of the light source is stabilized, the inner quality of vegetables and fruits cannot be measured and evaluated with good accuracy.

From the foregoing, in the conventional apparatuses, when the apparatuses are started, the warming-up operation has been obliged for a period of time obtained by multiplying the time considered to be necessary by the safety rate, that is, a long period of time more than that required. Further, when the apparatuses are restarted, and also when the apparatuses are returned after the power failure, the warning-up operation for a period of time similar to that when the apparatuses are first started has been obliged.

Therefore, when the apparatuses are first started, an operator has to wait for a long period of time more than that required till measurement and evaluation are started, and when the apparatuses are restarted, and when returned after the power failure, the time required for restart and a period of time for the power failure have not at all been taken into consideration, and therefore, the entirely wasteful time has been included in the waiting time.

Further, the above-described conventional apparatuses are all large in type and expensive, which measure and evaluate a large quantity of the same kind and the same breed of vegetables and fruits. Therefore, the spectral strength of the light source and the measuring time corresponding to vegetables and fruits have been set in advance, and the reflecting light or the transmission light from vegetables and fruits have been measured merely for the measuring time.

The conventional large type and expensive apparatuses have been difficult to be introduced by small enterprisers in terms of the installation place, purchase expenses or the like, and a small type and inexpensive apparatus has been demanded. On the other hand, for the small type and inexpensive apparatus, there is demanded general-purpose properties that can measure and evaluate many kinds and many breeds of vegetables and fruits.

However, the strength of the reflecting light or the transmission light from vegetables and fruits differs greatly depending on the kind or breed of vegetables and fruits. In a case of vegetables and fruits whose optical strength is small (absorbance is large), it is necessary to make the measuring time longer and maintain the S/N ratio in order to secure the measuring accuracy. Therefore, in a case where the measuring time is made to correspond to vegetables and fruits whose optical strength are small, the measuring time is surplus for vegetables and fruits whose optical strength are large.

On the other hand, in a case where the measuring time is made to correspond to vegetables and fruits whose optical strength is small, the resolution of an A/D converter has to be lowered in order to secure the dynamic range in the measurement of the optical strength, and when the resolution of an A/D converter is intended not to be lowered, an amplifier having a multistage gain is necessary.

The present invention has been accomplished in view of the problem as noted above with respect to prior art, and the object of the present invention is to provide a very convenient apparatus for evaluating the inner quality of vegetables and fruits, which is small in type and inexpensive, can be introduced easily by small-scaled enterprisers, can change the installation place easily, and in which measurement can be carried out easily, the measuring time can be shortened, and further, the safety and promptness in the replacing operation of a halogen lamp or the like as a light source are fully taken into consideration.

It is a further object of the present invention to provide a method for warming-up operating in the apparatus for evaluating the inner quality of vegetables and fruits in which the apparatus is subjected to the warming-up operation only for a sufficient period of time that required whereby the waiting time which is more than that required and is entirely wasteful is omitted while sufficiently securing the accuracy of measurement and evaluation to enable realization of the enhancement of operating efficiency and energy saving.

It is another object of the present invention to provide a method for measuring the inner quality in the apparatus for evaluating the inner quality of vegetables and fruits in which even if the kind and the breed of vegetables and fruits are variety, the inner quality can be measured efficiently while securing the sufficient measuring accuracy, and the apparatus constitution can be also simplified.

DISCLOSURE OF THE INVENTION

For achieving the aforementioned objects, an apparatus for evaluating the inner quality of vegetables and fruits according to the present invention comprises a place bed formed with a transmission light detecting hole and on which vegetables and fruits are placed; light sources disposed opposedly on both sides of the place bed to irradiate vegetables and fruits; a spectra/detection unit for making spectra in transmission light having transmitted through vegetables and fruits and passed through the transmission light detecting hole and detecting optical strength; an A/D converter for converting an analogue detection signal into a digital detection signal; an operation processing section for calculating and evaluating the quality evaluation amount of the sugar degree and the ripening degree on the basis of the detection signals; a measuring button for instructing the measurement; and a display panel for displaying the quality evaluation amount of the sugar degree and the ripening degree, the apparatus capable of being installed on the table, and also being portable.

Further, an apparatus for evaluating the inner quality of vegetables and fruits according to the present invention comprises a place bed formed with a transmission light detecting hole and on which vegetables and fruits are placed; light sources disposed opposedly on both sides of the place bed to irradiate vegetables and fruits; a spectra/detection unit for making spectra in transmission light having transmitted through vegetables and fruits and passed through the transmission light detecting hole and detecting optical strength; an A/D converter for converting an analogue detection signal into a digital detection signal; an operation processing section for calculating and evaluating the quality evaluation amount of the sugar degree and the ripening degree on the basis of the detection signals; a display panel for displaying the quality evaluation amount of the sugar degree and the ripening degree; and detection means for detecting whether or not vegetables and fruits are placed on the place bed, the apparatus capable of being installed on the table, and also being portable, wherein when the detection means detects that vegetables and fruits are placed on the place bed, the measurement is automatically started.

As the detection means, a position sensor or a weight sensor can be employed. Further, the strength of the transmission light can be measured preliminarily, and the detected optical strength can be compared. If a design is made so that when the placement of vegetables and fruits is detected, the measurement is automatically started, an operator is able to make measurement easily without troublesome operation, and the measuring time can be also shortened.

If a design is made so that the transmission light detecting hole and the spectra/detection unit are connected by optical fibers, it is possible to prevent the stray light from entering and to enhance the measuring accuracy, which is preferable.

If the place bed is formed with a fitting depressed portion on which vegetables and fruits are placed, and the fitting depressed portion is formed with a transmission light detecting hole extending to the bottom, vegetables and fruits can be held on the fitting depressed portion stably to enable positive measurement, which is preferable.

Further, if a holding material comprising a sponge rubber is installed on the fitting depressed portion of the place bed, it comes to close contact with vegetables and fruits due to the flexibility of the holding material to prevent the stray light from entering the transmission light detecting hole, thus enhancing the measuring accuracy, which is preferable.

If the spectra/detection unit is designed so that the transmission light having transmitted through vegetables and fruits is divided into a number of frequency areas to detect the optical strength of each frequency area, various quality evaluation amounts can be calculated from the optical strength of each frequency area, which is preferable.

If a shutter opening and closing device comprising a shutter for shielding light having passed through the transmission light detecting hole and a shutter driving device for moving the shutter is disposed, the measurement in the shield time can be automated, which is preferable.

If a transmission standard body setting device comprising a transmission standard body for transmitting light having passed through the transmission light detecting hole and a transmission standard body driving device for moving the transmission standard body is disposed, the measurement of the standard body can be automated, which is preferable.

Further, if a peripheral temperature of a light source is detected in a manner of a lapse of time, the peripheral temperature of a light source is compared with a safety setting temperature, and the fact that the light source temperature is completely lowered is reported, the replacing operation of the light source can be carried out safely and promptly.

Further, if an environment temperature is detected in a manner of a lapse of time, and the peripheral temperature of a light source is also compared with the environment temperature whereby the fact that the light source temperature is completely lowered is reported, it can cope with even the difference in the environment conditions such as the summer season, the tropical zone or the like.

A method for warming-up operating in an apparatus for evaluating the inner quality of vegetables and fruits according to the present invention comprises: automatically judging that a spectra of a light source is stabilized to decide the termination of the warming-up operation, and executing the warming-up operation till the termination of the warming-up operation.

Further, a method for a warming-up operating in an apparatus for evaluating the inner quality of vegetables and fruits according to the present invention comprises: automatically judging that a spectra of a light source is stabilized to decide the termination of the warming-up operation, executing the warming-up operation without operating a light source cooling fan till the termination of the warming-up operation, and operating the light source cooling fan after the termination of the warming-up operation.

Alternatively, the spectra of the light source is detected in a manner of a lapse of time, whether or not the spectra of the light source is stabilized is judged by the strength ratio of light or the strength difference of light of a fixed wavelength, and the termination of the warming up operation is decided.

Further, alternatively, the peripheral temperature of the light source is detected in a manner of a lapse of time, whether or not the spectra of the light source is stabilized is judged on the basis of the fact that the peripheral temperature is stabilized, and the termination of the warming-up operation is decided.

In a case where the peripheral temperature of the light source is detected in a manner of a lapse of time, a fixed time ts is added after the stabilization of the peripheral temperature to thereby decide the termination of the warming-up operation.

It is preferably confirmed that the strength of light having a fixed wavelength be within the allowable range to decide the termination of the warming-up operation.

A method for measuring the inner quality in an apparatus for evaluating the inner quality of vegetables and fruits according to the present invention comprises: preliminarily measuring the strength of light having reflected or transmitted through vegetables and fruits in a relatively short period of time before the inner quality of vegetables and fruits is measured really, setting the time for measuring the inner quality corresponding to the strength of light measured, measuring the strength of light having reflected or transmitted through vegetables and fruits in the measuring time set, and measuring the inner quality really.

Alternatively, a table corresponding the measuring time necessary in the real measurement to the strength of light measured in the preliminary measurement is set, the measured value of the strength of light is collated to the table, and the measuring time necessary in the real measurement is set.

Preferably, as the strength of light in the preliminary measurement, the strength of light having a fixed wavelength is employed.

Particularly, preferably, as the fixed wavelength, a wavelength within the range of 700~850 nm is employed.

BRIEF DESCRIPTION OF THE DRAWINGS

FIGS. 19(A) and 19(B) show the interior of an apparatus for evaluating the inner quality of vegetables and fruits according to a further embodiment of the present invention, (A) being a plan view, (B) being a front view.

FIG. 35 is an explanatory view showing a table in which the measuring time T necessary in the real measurement is made to correspond to the optical strength P measured in the preliminary measurement.

BEST MODE FOR CARRYING OUT THE INVENTION

The preferred embodiments of the apparatus for evaluating the inner quality of vegetables and fruits according to the present invention will be described hereinafter with reference to the drawings.

The apparatus for evaluating the inner quality of vegetables and fruits 1 according to one embodiment of the present invention is a small and light-weight apparatus which can be placed on a table, and is portable, having approximately the width of 530 mm, the depth of 343 mm, and the height of 280 mm, as shown in FIGS. 1 to 4, in which a place bed 3 is disposed substantially in the central portion on a casing 2, and light sources 4, 4 are opposedly disposed on both sides of the place bed 3.

Figure 4:
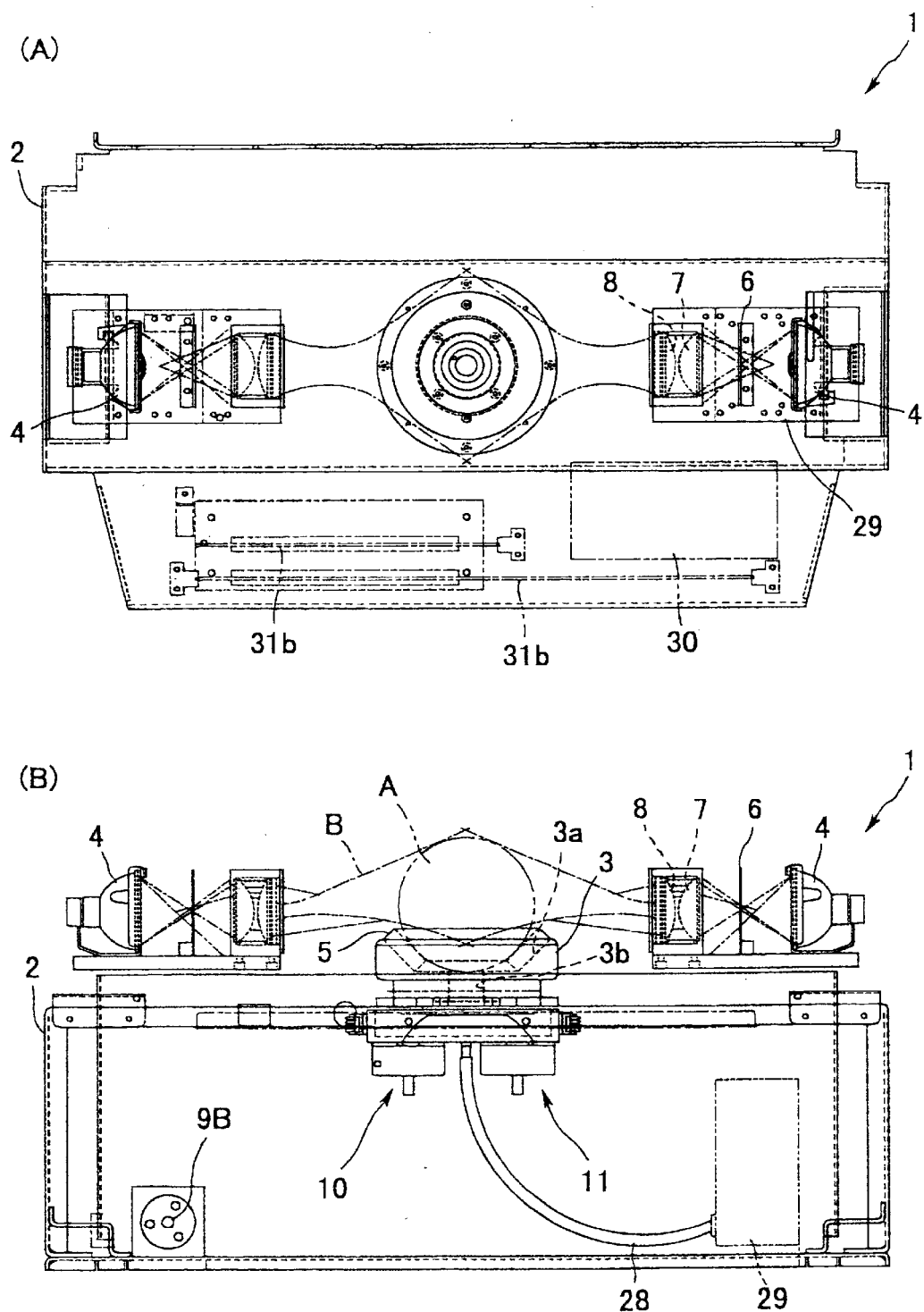
FIGS. 4(A) and 4(B) show the interior of the apparatus for evaluating the inner quality of vegetables and fruits of the present invention, (A) being a plan view, (B) being a front view.

As shown in FIG. 4, the place bed 3 is formed at the upper part with a fitting depressed portion 3a having an inner surface in the form of an inverted conical curved surface, and a transmission light detecting hole 3b extending to the bottom is formed substantially in the central portion of the fitting depressed portion 3a. An inverted conical annular holding material 5 formed of sponge rubber is fitted in the fitting depressed portion 3a of the placed bed 3, the holding material 5 is obtained by foaming semi-independently and semi-continuously synthetic rubber such as ethylene-propylene ter-polymer (EPDM) to form a porous construction.

Since the fitting depressed portion 3a is formed in the place bed 3, and the holding material 5 formed of sponge rubber is fitted in the fitting depressed portion 3a, vegetables and fruits A can be held on the place bed 3 stably, and the vegetables and fruits A is placed in close contact with the holding material 5 due to the flexibility of the holding material 5 to prevent stray light from entering the transmission light detecting hole 3b, whereby measurement can be accomplished stably and with high accuracy.

Figure 5:
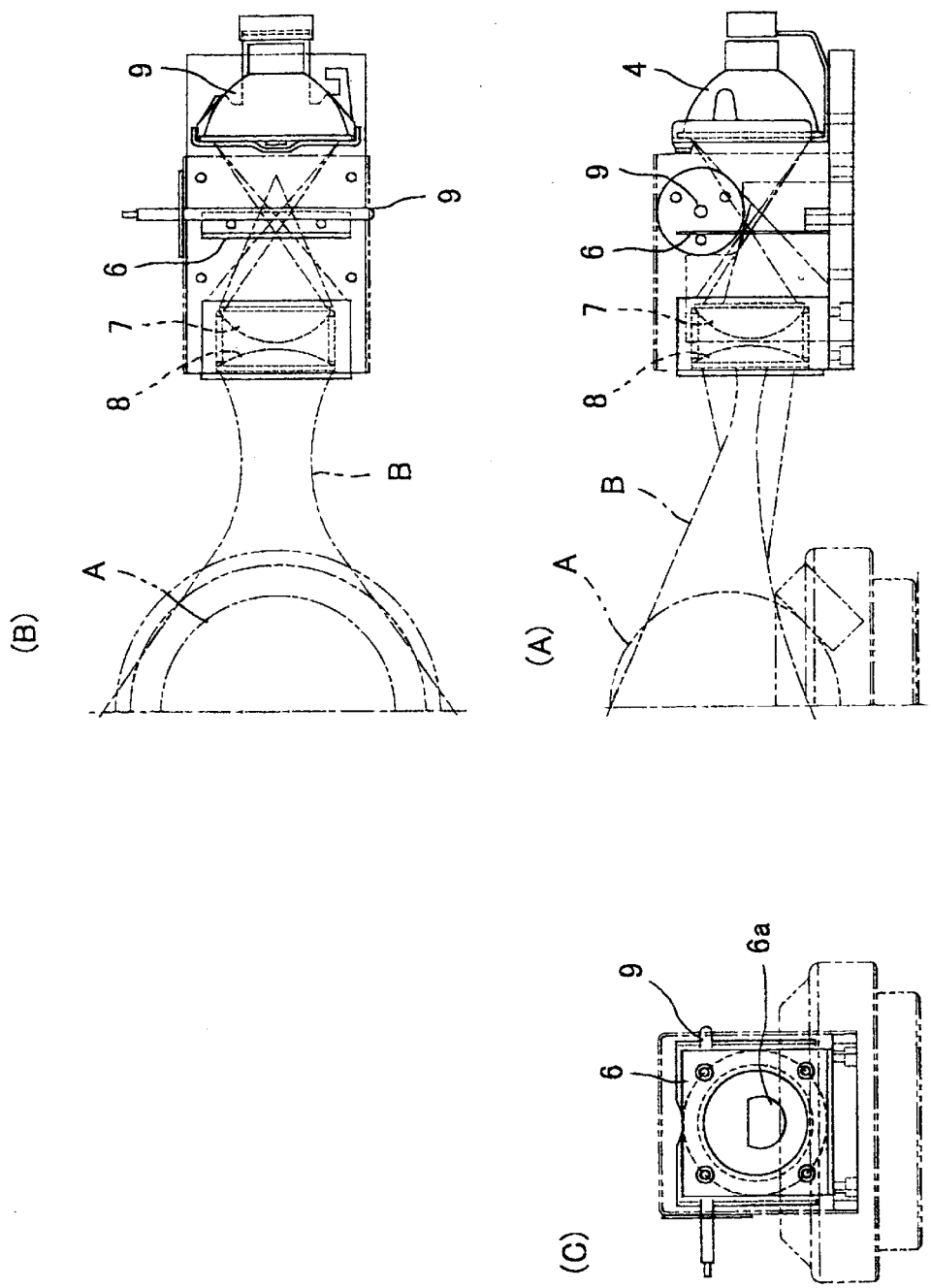
FIG. 5(A), FIGS. 5(B) and 5(C) show the neighborhood of a light source of the apparatus for evaluating the inner quality of vegetables and fruits of the present invention, (A) being a front view, (B) being a plan view, (C) being a side view.

As the light sources 4, 4, halogen lamps are used, and a slit plate 6 and lenses 7, 8 are arranged forward of the light sources 4, 4, as shown in FIG. 5.

The slit plate 6 is formed with a substantially semicircular slit 6a, and the lenses 7 and 8 comprises an aspherical condenser lens and a spherical convex lens, whose curved surfaces are opposed.

In this manner, the light quantity of irradiation light B is sufficiently secured, the light moving downward is diffused while removing it suitably, and in the state that the vegetables and fruits A is placed on the place bed 3, the irradiation light B impinges upon both sides of the vegetables and fruits A.

A temperature sensor 9A comprising a thermister is arranged between the light source 4 and the slit plate 6.

The temperature around the light sources 4, 4 is detected by the temperature sensor 9A whereby the time necessary for the warming-up operation to be executed to stabilize the measuring accuracy of the apparatus for evaluating the inner quality of vegetables and fruits 1 can be calculated automatically. The temperature of the light sources 4, 4 themselves may be measured directly by the temperature sensor 9A.

Further, by detecting the temperature around the light sources 4, 4, whether or not the circumference of the light sources 4, 4 becomes a safety temperature can be informed at the time of replacing the halogen lamp.

Further, as shown in FIG. 4, a separate temperature sensor 9B comprising a thermister is arranged at a suitable position within the casing 2 considerably away from the light sources 4, 4, that is, at a position affected by the temperature of the light sources as less as possible.

By detecting the environment temperature by the temperature sensor 9B, there can be provided one reference for judging whether or not the circumference of the light sources 4, 4 becomes a safety temperature at the time of replacing the halogen lamp.

A shutter opening and closing device 10 and a transmission standard body setting device 11 are disposed within the casing 2 directly below the place bed 3.

Figure 6:
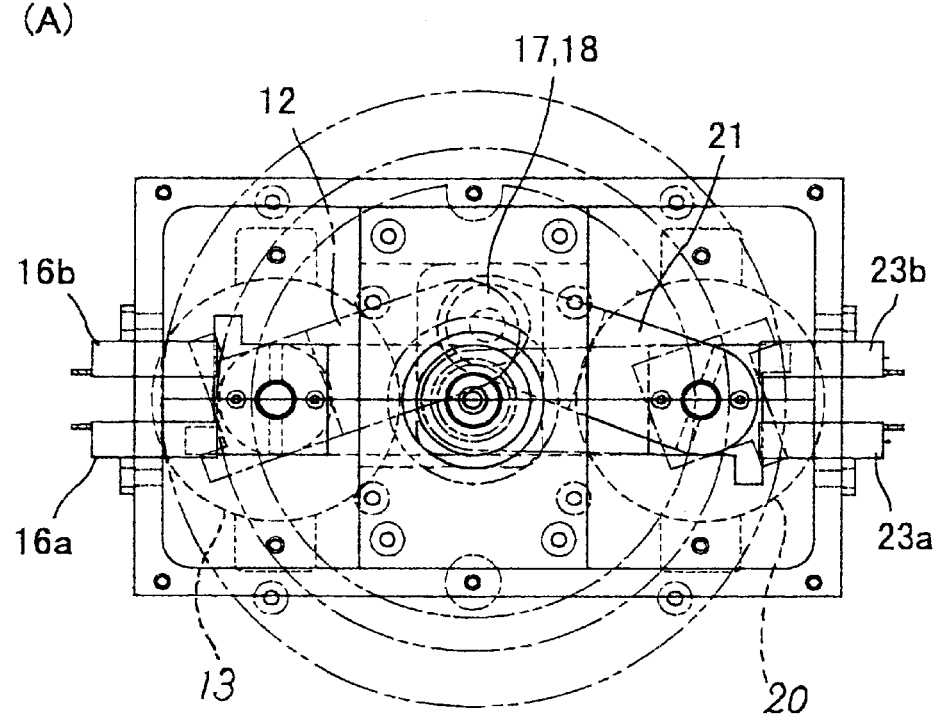
FIGS. 6(A) and 6(B) show a shutter opening and closing device and a transmission standard body setting device of the apparatus for evaluating the inner quality of vegetables and fruits of the present invention, (A) being a plan view, (B) being a front view.
Figure 6:
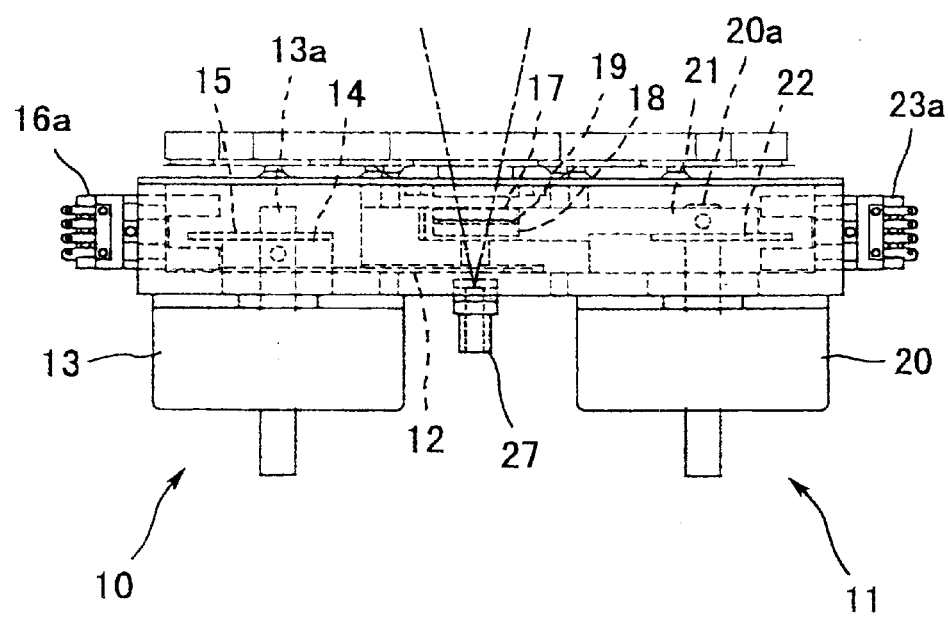
Figure 7:
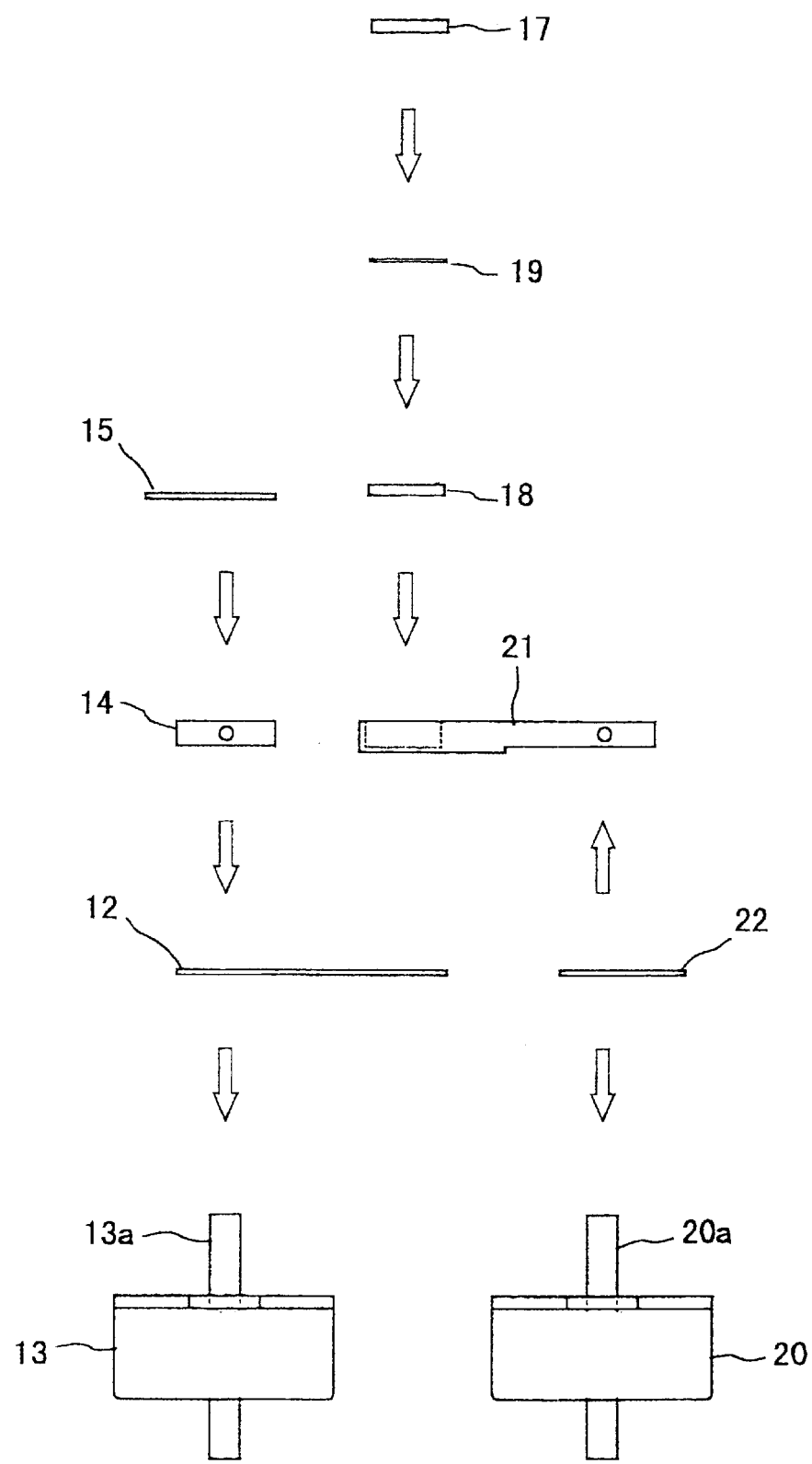
FIG. 7 is an exploded explanatory view of a shutter opening and closing device and a transmission standard body setting device of the apparatus for evaluating the inner quality of vegetables and fruits of the present invention.

The shutter opening and closing device 10 comprises, as shown in FIGS. 6 and 7, a shutter 12, a shutter drive device 13 formed from a rotary solenoid, a stationary member 14, and a position detecting plate 15, the shutter 12 and the position detecting plate 15 being secured to a shaft 13a of the shutter drive device 13 through the stationary member 14.

The shutter 12 is a thin plate coated with black, and is rotated at a fixed angle by the shutter drive device 13 to cut off transmission light C having passed through the transmission light detecting hole 3b.

Further, position sensors 16a, 16b are disposed, which detect a position of the position detecting plate 15 to thereby inform whether or not the shutter 12 is closed.

The transmission standard body setting device 11 comprises, as shown in FIGS. 6 and 7, transmission standard bodies 17, 18, a spacer 19, a transmission standard body drive device 20 formed from a rotary solenoid, a support member 21, and a position detecting plate 22, the transmission standard bodies 17, 18 being installed on the support member 21 through the spacer 19, the position detecting plate 22 being secured to the shaft 20a of the transmission standard body drive device 20 through the support member 21.

The transmission standard body 17 is a silicon glass plate having an upper surface formed into a sattin finished surface by sand blasting, which performs a function as a diffusion plate not to allow the transmission light C have directivity, and the transmission standard body 18 is a silicon glass plate having an upper surface in the form of a vaporized surface by way of chrome, which performs a function as an adjusting plate for suitably adjusting the light quantity of the transmission light C.

The transmission standard bodies 17, 18 are rotated at a fixed angle by the transmission standard body drive device 20 to convert the transmission light C having passed through the transmission light detecting hole 3b into the light having the feature similar to the light having transmitted through the vegetables and fruits A as an article to be tested.

Further, position sensors 23a, 23b are disposed, which detect a position of the position detecting plate 22 to thereby inform whether or not the transmission standard bodies 17, 18 are set.

Figure 1:
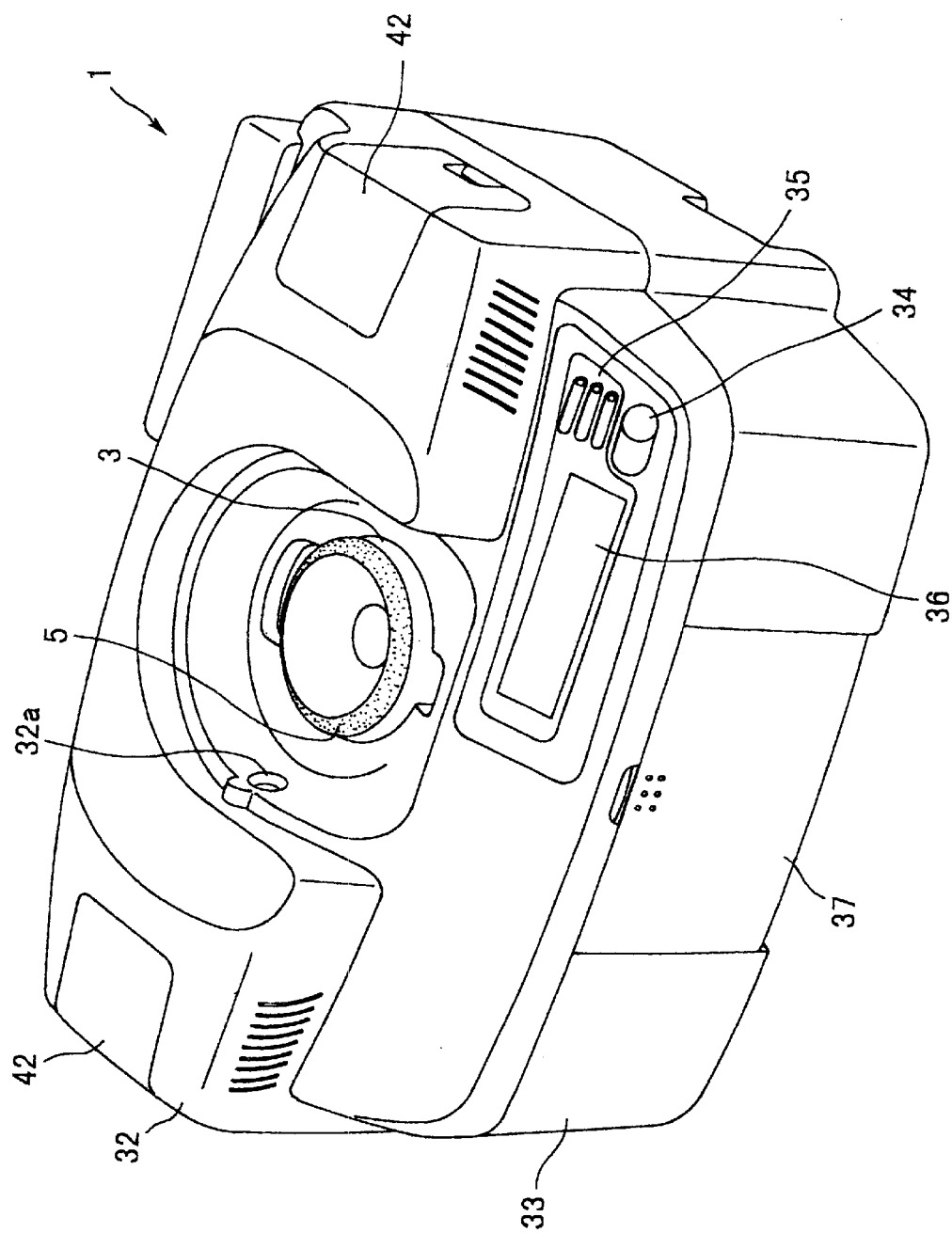
FIG. 1 is an external perspective view of an apparatus for evaluating the inner quality of vegetables and fruits according to one embodiment of the present invention.
Figure 2:
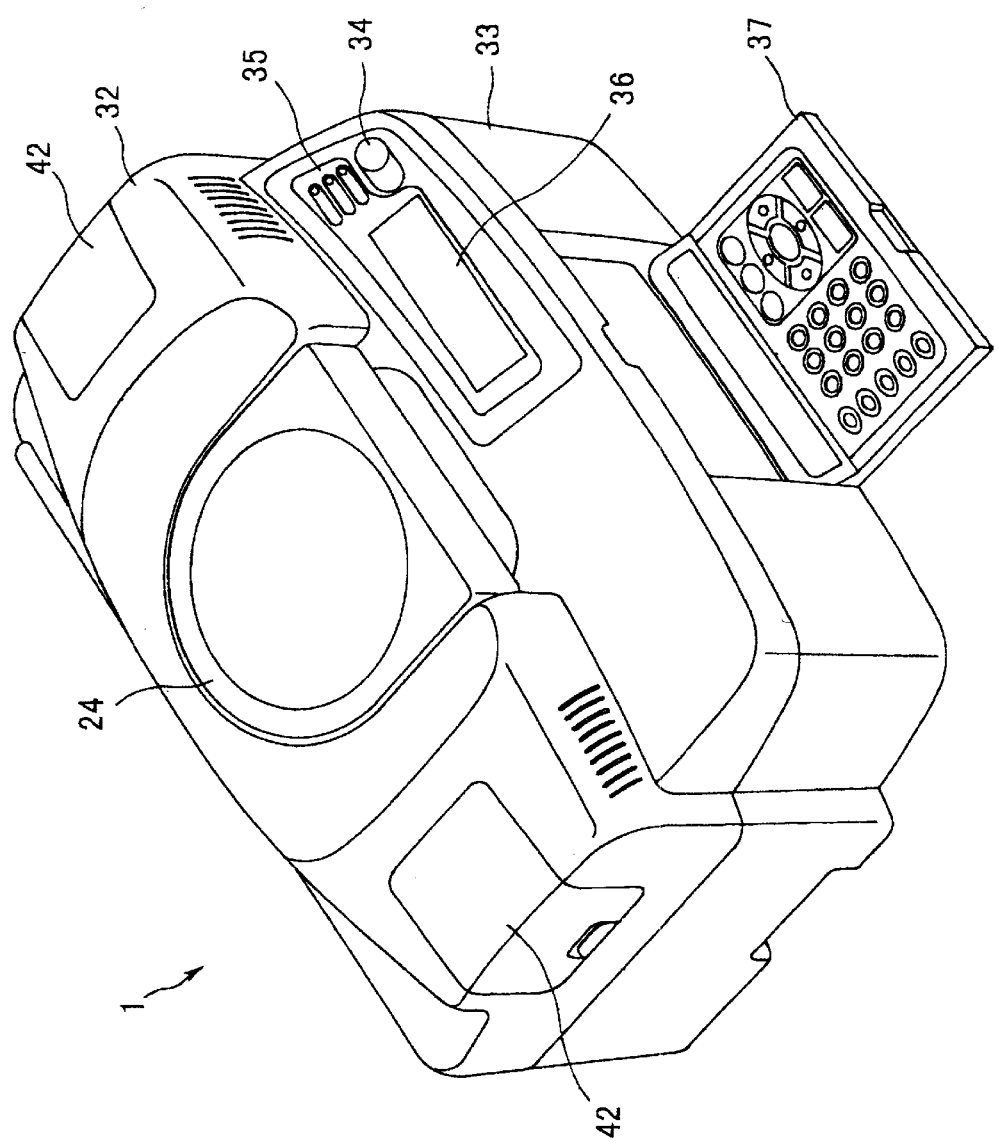
FIG. 2 is an external perspective view of an apparatus for evaluating the inner quality of vegetables and fruits of the present invention in the state that an operating panel is opened, and a correcting cover is installed.
Figure 3:
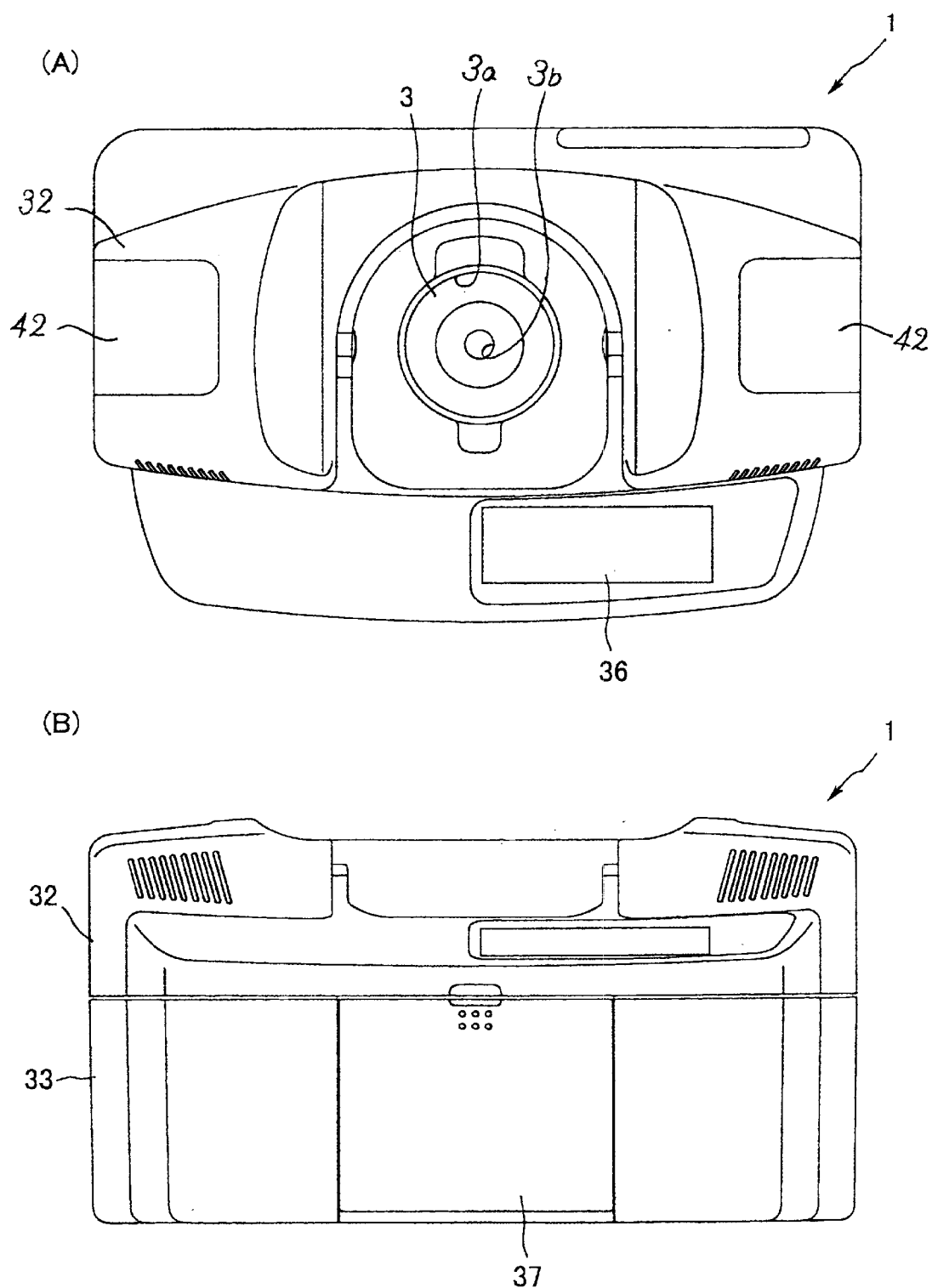
FIGS. 3(A) and 3(B) show the external appearance of the apparatus for evaluating the inner quality of vegetables and fruits of the present invention, (A) being a plan view, (B) being a front view.
Figure 8:
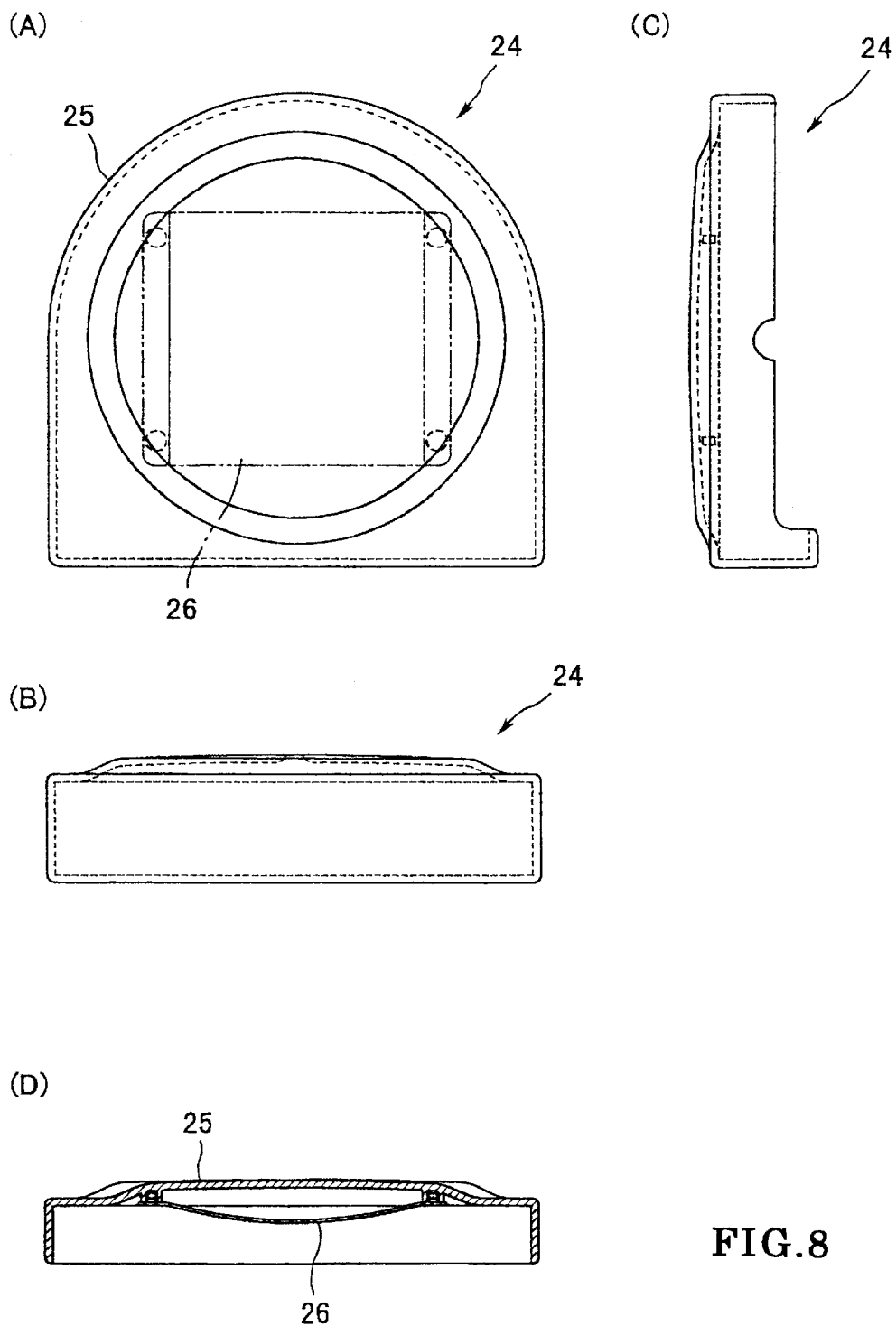
FIGS. 8(A), 8(B), 8(C) and 8(D) show a correcting cover of the apparatus for evaluating the inner quality of vegetables and fruits of the present invention, (A) being a plan view, (B) being a front view, (C) being a side view, (D) being a sectional view.

The apparatus for evaluating the inner quality of vegetables and fruits 1 has a correcting cover 24 attached thereto used when the apparatus is corrected periodically, as shown in FIGS. 2 and 8. The correcting cover 24 is a cover in which a reflecting standard body 26 is secured to the lower surface internally of a lid cover 25.

The reflecting standard body 26 is a thin plate formed into a curved surface and coated with white color, in which when the correcting cover 24 is installed, it is positioned above the place bed 3 to reflect the irradiation light B from the light sources 4, 4 so as to guide it to the transmission light detecting hole 3b.

A light receiving member 27 is disposed below the transmission light detecting hole 3b. One end of the optical fiber 28 is connected to the light receiving member 27, and the other end is connected to a spectra/detection unit 29 so as to guide the transmission light C to the spectra/detection unit 29.

As described above, if the transmission light detecting hole 3b and the spectra/detection unit 29 are connected by the optical fiber 28, it is possible to prevent the stray light from entering, thus enabling enhancement of the measuring accuracy.

Within the casing 2 are disposed, as shown in FIG. 4, a spectra/detection unit 29, an A/D converter 30, and an operation processing unit 31 comprising two PC plates 31a, 31b.

The spectra/detection unit 29 is provided to divide the transmission light C having passed through the optical fiber 28 into a number of frequency areas to detect the optical strength of each frequency area and output it as a voltage signal.

The A/D converter 30 is provided to convert an analogue detection signal from the spectra/detection unit 29 and the temperature sensor 9 into a digital detection signal.

The operation processing unit 31 is provided to calculate the quality evaluation amount of the sugar degree, the ripening degree or the like on the basis of a detection signal of the optical strength to evaluate the inner quality, or calculate the warming-up operation time on the basis of a detection signal of a temperature around the light sources 4, 4 to judge the termination time of the warming-up operation, or set the real measuring time of the optical strength on the basis of a preliminary detection value of the optical strength to execute processing of various data, input/output control or the like.

Figure 9:
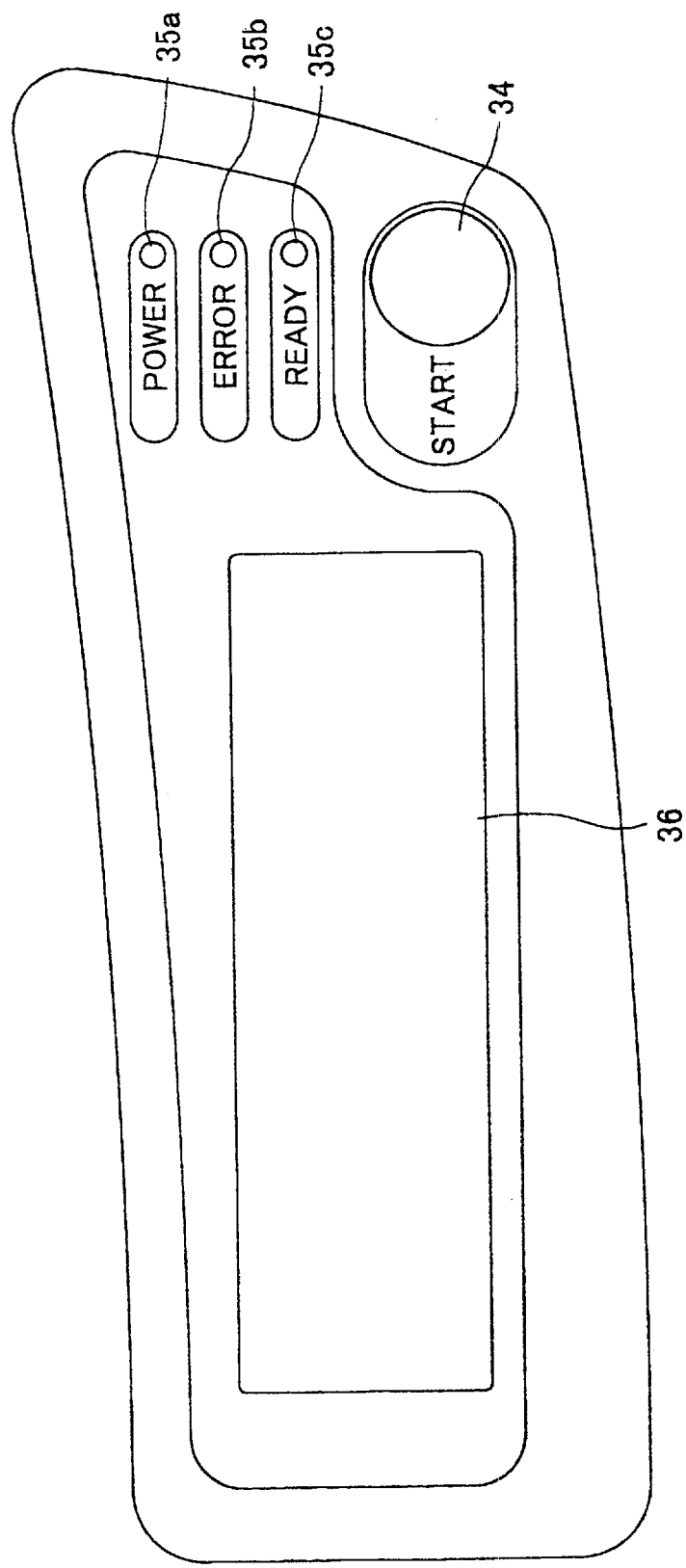
FIG. 9 is a plan view of a display panel of the apparatus for evaluating the inner quality of vegetables and fruits of the present invention.

The casing 2 is covered by upper and lower covers 32, 33, and on the front side of the upper surface of the upper cover 32 are disposed, as shown in FIG. 9, a measuring button 34, various display lamps 35 comprising a light emitting diode (LED), and a display panel 36 comprising a liquid crystal display (LCD).

As the display lamps 35, there are disposed a power supply display lamp 35a, an error display lamp 35b, and a measurement-ready completion display lamp 35c.

On the display panel 36 are displayed the setting mode mentioned below, the quality evaluation amounts such as the sugar degree, the ripening degree, the honey amount or the degree of changing into brown, or the error code or the like by letters or numerical values.

On the display panel 36 are also displayed the warming-up operation state or the measurable state. In addition, the temperature around the light sources 4, 4, or the alarm indicating a high temperature may be also displayed.

Figure 10:
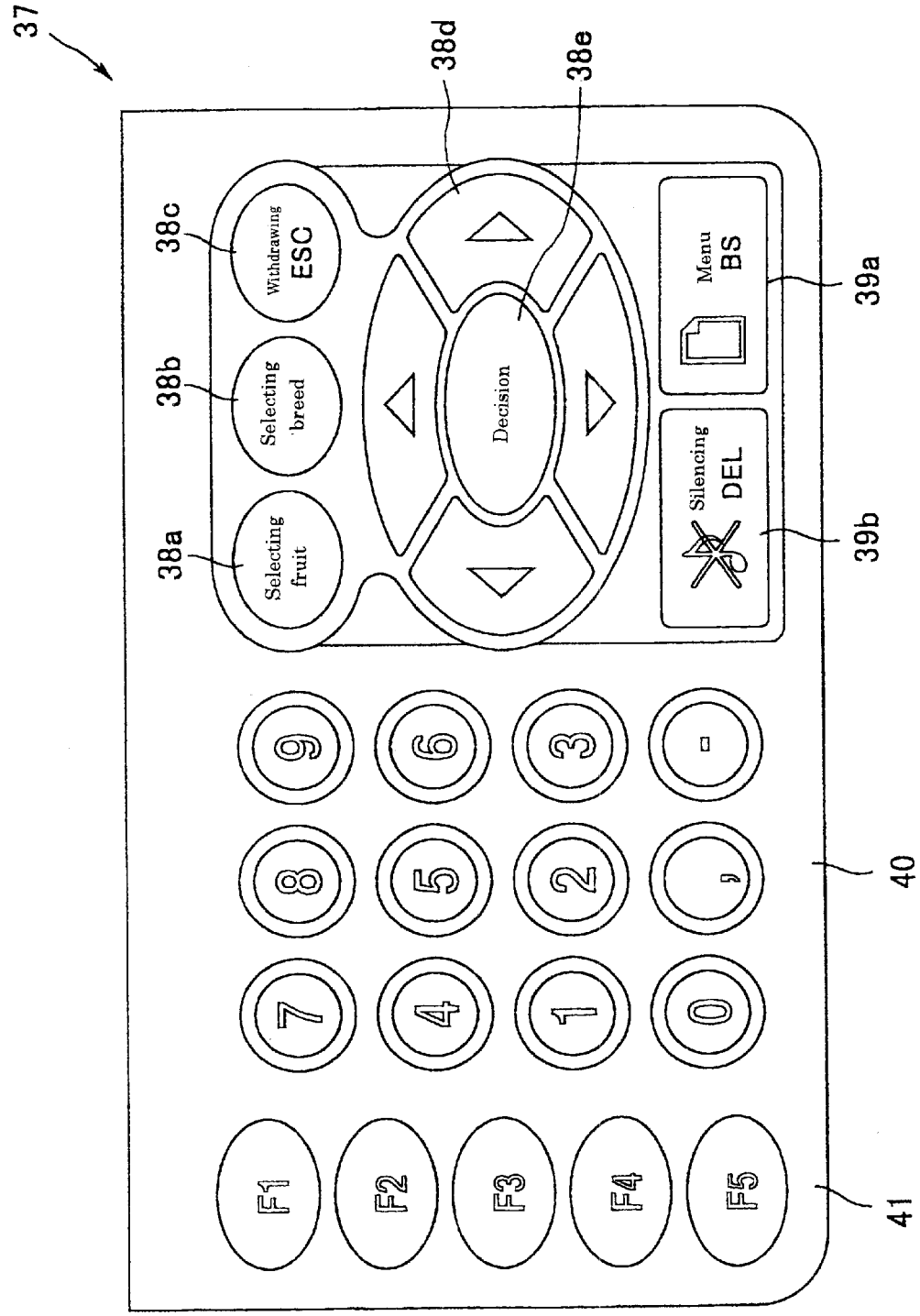
FIG. 10 is a plan view of an operating panel of the apparatus for evaluating the inner quality of vegetables and fruits of the present invention.

In the central portion of the front surface of the lower cover 33 is disposed a closable operating panel 37, as shown in FIG. 2, and as shown in FIG. 10, on the operating panel 37 are disposed various operating buttons such as mode selecting buttons 38, environment setting buttons 39, ten keys 40, and function keys 41.

As the mode selecting buttons 38, there are disposed a fruit selecting button 38a for selecting the kind of fruits such as apple, orange or the like, a breed selecting button 38b for selecting the breed of fruits such as Fuji or Kokko, a withdrawing button 38c for returning to the previous screen, a scroll button 38d for the scrolling on the screen, and a deciding button 38e for deciding the mode.

As the environment setting buttons 39, there are disposed a menu button 39a for changing the measuring mode or the date mode, and a silencing button 39b for silencing various error buzzers. By changing the measuring mode, the automatic measurement or the manual measurement can be selected.

The upper cover 32 is formed in both inner surfaces of a central cave-in portion with irradiation light passing-through holes 32a, 32a, and the irradiation light B from the light sources 4, 4 moves outside of the upper cover 32 from the irradiation light passing-through holes 32a, 32a so as to impinge upon the vegetables and fruits A placed on the place bed 3.

Further, on both sides of the upper cover 32 are disposed light source covers 42, 42 that are detachably mounted, and the light source covers 42, 42 are removed whereby the light sources 4, 4 can be exchanged easily.

The operation control unit 31 issues an alarm by way of an alarm buzzer if the light source covers 42, 42 are removed when the temperature detected by way of the temperature sensor 9 exceeds a set temperature.

Next, the operation and the effect of the apparatus for evaluating the inner quality of vegetables and fruits 1 according to the present invention will be explained along with the using method with reference to FIGS. 11 to 16.

First, when a power supply button (not shown) disposed on the back of the apparatus for evaluating the inner quality of vegetables and fruits 1 is pressed down to turn on the power supply, the power supply display lamp 35*a* lights, the light sources 4, 4 start to emit light, and the warming-up operating state is displayed on the display panel 36.

The warming-up operating state continues and when the temperature sensor 9A detects that the temperature around the light sources 4, 4 reaches the fixed temperature, the termination of the warming-up operation is displayed on the display panel 36.

Figure 14:
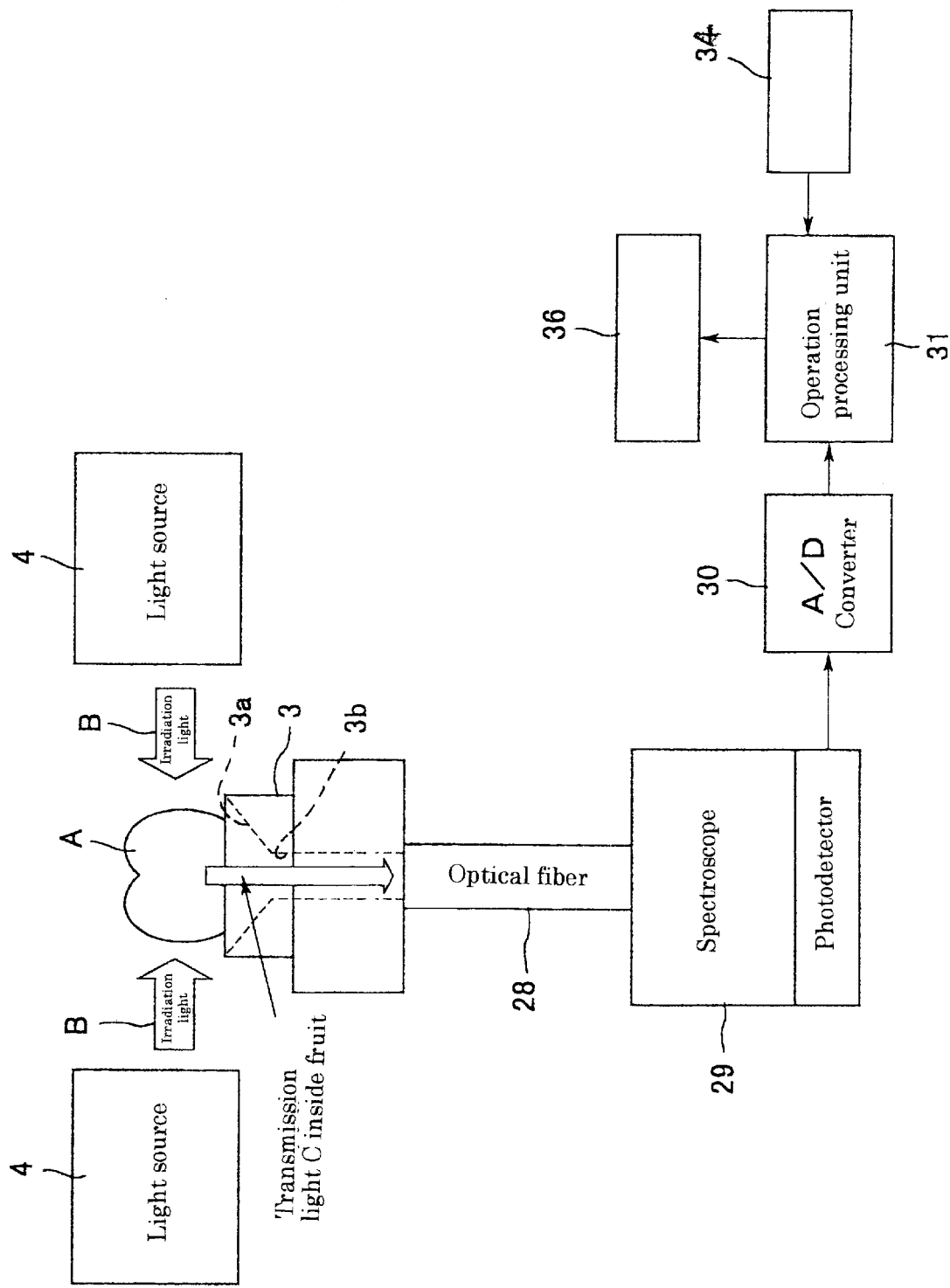
FIG. 14 is a schematic explanatory view showing the vegetables and fruits measuring state in the apparatus for evaluating the inner quality of vegetables and fruits of the present invention.

Then, the shutter drive device 13 is automatically actuated, the shutter 12 is rotated, and as shown in FIG. 14, the external light including the irradiation light B from the light sources 4, 4 is cut off, and the shading measuring state is displayed on the display panel 36.

In the shading measuring state, the internally residual voltage in the optical fiber 28, the spectra/detection unit 29 or the like is measured by the spectra/detection unit 29. Here, since the frequency area is divided into 256, internally residual voltage data D (1)~D (256) are to be obtained.

When the shading time measurement is completed, the completion of the shading time measurement is displayed on the display panel 36, and the instructions for installing the correcting cover 24 is displayed.

Figure 15:
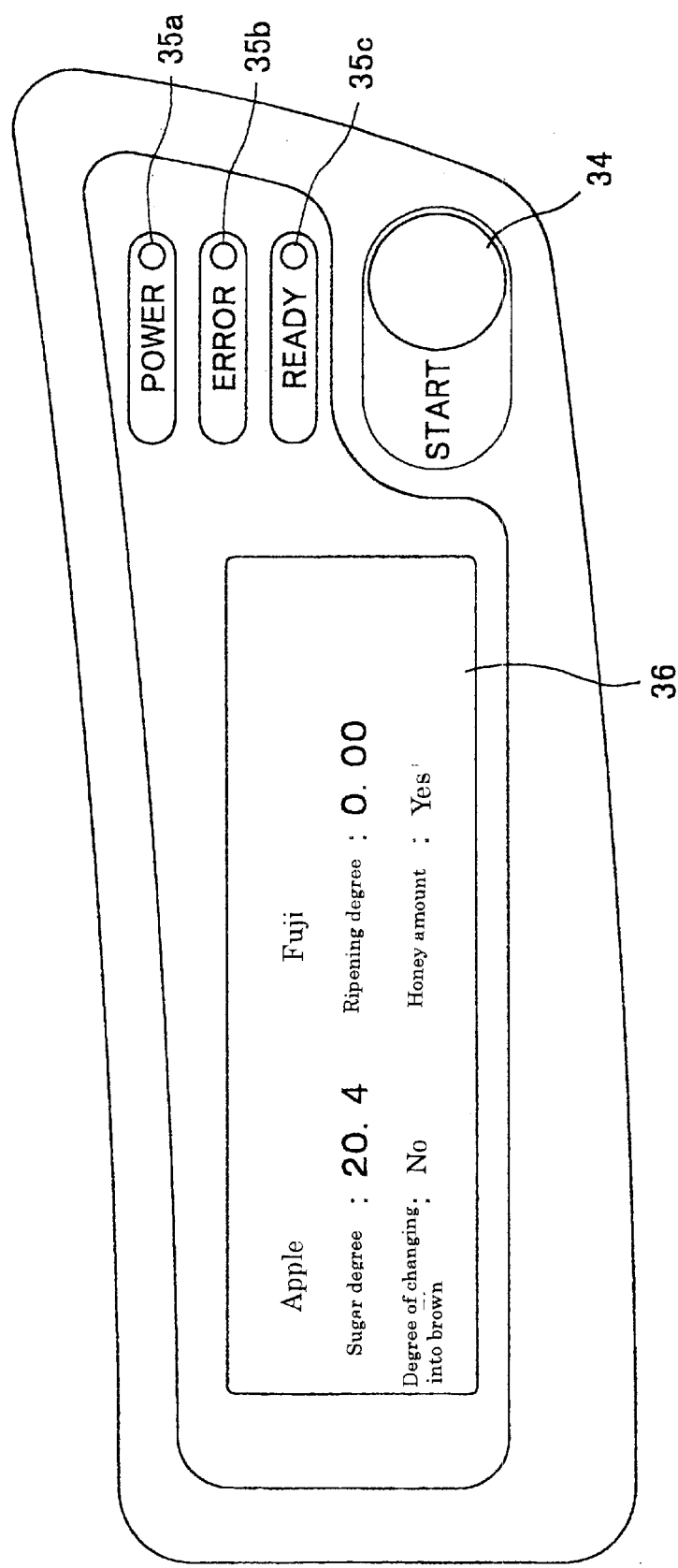
FIG. 15 is a plan view showing the state that the quantity evaluation amount is displayed on a display panel in the apparatus for evaluating the inner quality of vegetables and fruits of the present invention.

When an operator installs the correcting cover 24, which was detected by a position sensor (not shown), the transmission standard body drive device 20 is automatically actuated to rotate the transmission standard bodies 17, 18, and as shown in FIG. 15, the irradiation light B from the light sources 4, 4 is reflected by the reflecting standard body 26, passes through the transmission light detecting hole 3*b*, passes through the transmission standard bodies 17, 18 into the transmission light C, which passes through the optical fiber 28 and is guided to the spectra/detection unit 29, and the standard body measuring state is displayed on the display panel 36.

In the standard body measuring state, the transmission light C is divided into a number of frequency areas by the spectra/detection unit 29, and the optical strength of every frequency area is measured. Here, since the frequency area is divided into 256, optical strength data R (1)~R (256) are to be obtained.

When the standard body measurement is completed, the measurement ready completion display lamp 35*c* is lighted to display the completion of the standard body measurement on the display panel 36 and display the vegetables and fruits measurable state.

When an operator revolts against the correcting cover 24 to place the vegetables and fruits A on the place bed 3 and press down the measuring button 34, as shown in FIG. 14, the irradiation light B from the light sources 4, 4 transmits through the vegetables and fruits A into the transmission light C, which passes through the transmission light detecting hole 3*b* and the optical fiber 28 and is guided to the spectra/detection unit 29, and the vegetables and fruits measuring state is displayed on the display panel 36.

In the vegetables and fruits measuring state, the transmission light C is divided into a number of frequency areas by the spectra/detection unit 29, and the optical strength of every frequency area is measured. Here, since the frequency area is divided into 256, optical strength data S (1)~S (256) are to be obtained.

When the vegetables and fruits measurement is completed, the absorbance of every frequency area caused by the vegetables and fruits A is calculated as the ABS (1)~ABS (256) from the optical strength data S (1)~S (256), R (1)~R (256), and the internally residual voltage data D (1)~D (256) by the operation processing unit 31.

The quality evaluation amounts such as the sugar degree, the ripening degree, the honey amount, and the degree of changing into brown are calculated or decided from the absorbance data ABS (1)~ABS (256), and are displayed on the display panel 36, as shown in FIG. 15, by letters or numerical values along with the kind and the breed of vegetables and fruits.

Next, a description will be made of a case where in any of the states of the warming-up operation, the shading time measurement, the standard body measurement and the vegetables and fruits measurement, halogen lamps as the light sources 4, 4 are broken due to the service life, the over-current or the like.

When a power supply button (not shown) is pressed down to turn on the power supply, the light sources 4, 4 start to emit light, and the temperature sensor 9A detects the temperature around the light source 4 and the temperature sensor 9B detects the environment temperature.

Figure 16:
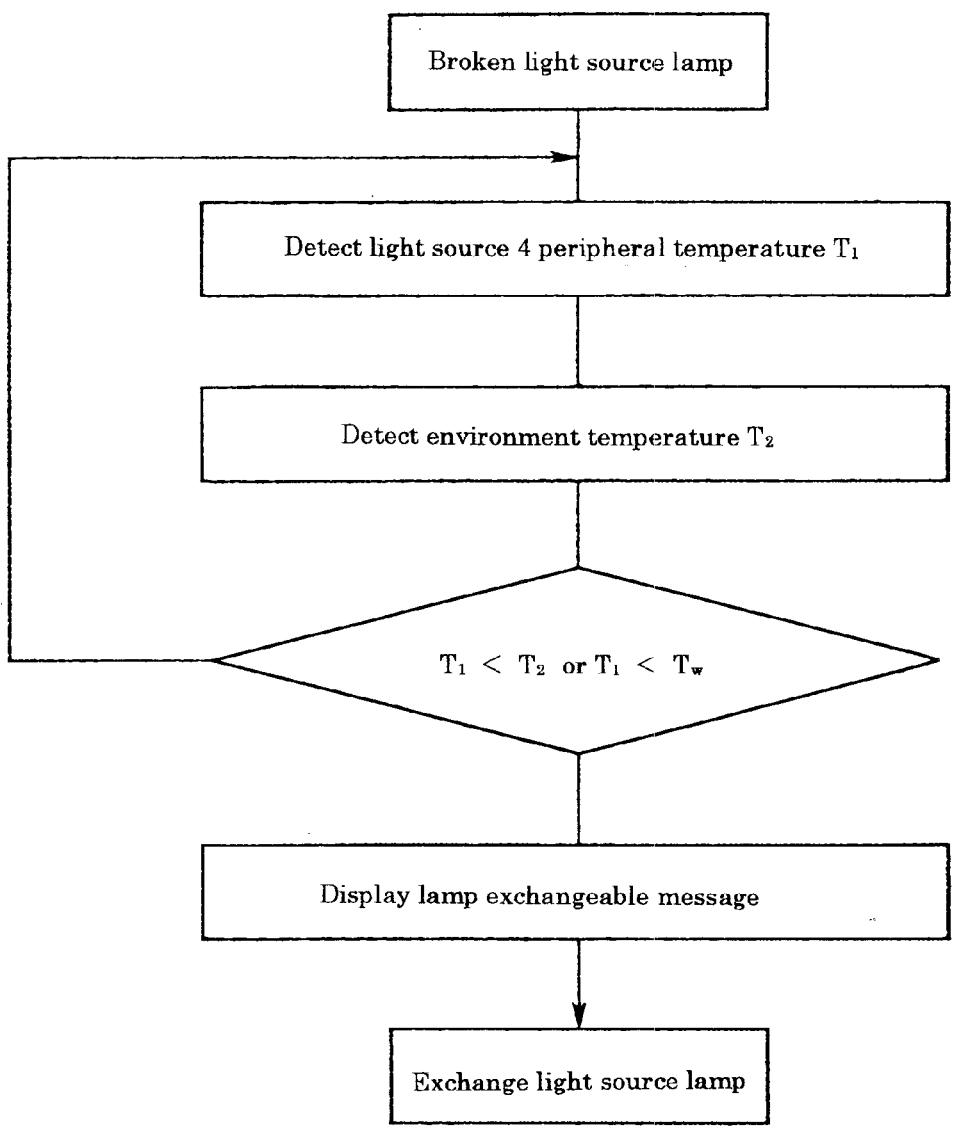
FIG. 16 is a process (step) view showing the light source exchanging procedure in the apparatus for evaluating the inner quality of vegetables and fruits of the present invention.

The operation processing unit 31, as shown in FIG. 16, always takes in the detected light source peripheral temperature $T_1$ and the environment temperature $T_2$ as data to compare the light source peripheral temperature $T_1$ with the environment temperature $T_2$ or the safety setting temperature $T_w$.

The safety setting temperature $T_w$ is stored in advance in the operation processing unit 31, and for example, even if the difference between the light source temperature and the light source peripheral temperature $T_1$ is taken into consideration and even if the operator touches a halogen lamp as the light source 4, a safety temperature of 25° C. is selected.

If the halogen lamp becomes broken, the light source peripheral temperature $T_1$ gradually lowers, and when $T_1$ and $T_w$ are in a relation of $T_1 < T_w$, even if the halogen lamp is touched, the temperature is at a degree to the extent not to get burn, therefore, the state that the lamp can be exchanged is displayed on the display panel 36.

Further, in the summer season or in the tropical zone, since the environment temperature $T_2$ sometimes exceeds the safety setting temperature $T_w$, even at the time of $T_1 < T_2$, the state that the lamp can be exchanged is displayed on the display panel 36.

The operator confirms the lamp exchangeable message, and afterward, removes the light source covers 42, 42 to replace the halogen lamps as the light sources 4, 4.

It can be designed so that in a case where not in the state of $T_1 < T_w$ or $T_1 < T_2$, the light source covers 42, 42 are removed, a buzzer may ring. Even this may inform the operator that a danger is present.

As described above, if the light source peripheral temperature $T_1$ and the environment temperature $T_2$ are detected, and the light source peripheral temperature $T_1$ is compared with the environment temperature $T_2$ or the safety setting temperature $T_w$ at all times, the state that the temperatures of the halogen lamps as the light sources 4, 4 are fully lowered can be informed to enable the exchanging operation of the halogen lamps safety, and the avoidance of the waiting more than as needed to waste the time.

The apparatus for evaluating the inner quality of vegetables and fruits 1 according to the present invention is constituted such that the place bed, the light sources, the spectra/detection unit, the operation processing unit, the operating button, the display panel or the like are enveloped compactly, can be installed on the table, and is portable, thus being small and inexpensive, and can be easily introduced even the small enterprisers. Further, the installation place can be changed easily, which is very convenient.

Further, the apparatus for evaluating the inner quality of vegetables and fruits 1 according to the present invention detects the light source peripheral temperature so as to inform the state that the temperature of the light source is fully lowered, therefore, the exchanging operation of the light sources can be accomplished safely and promptly.

Figure 17:
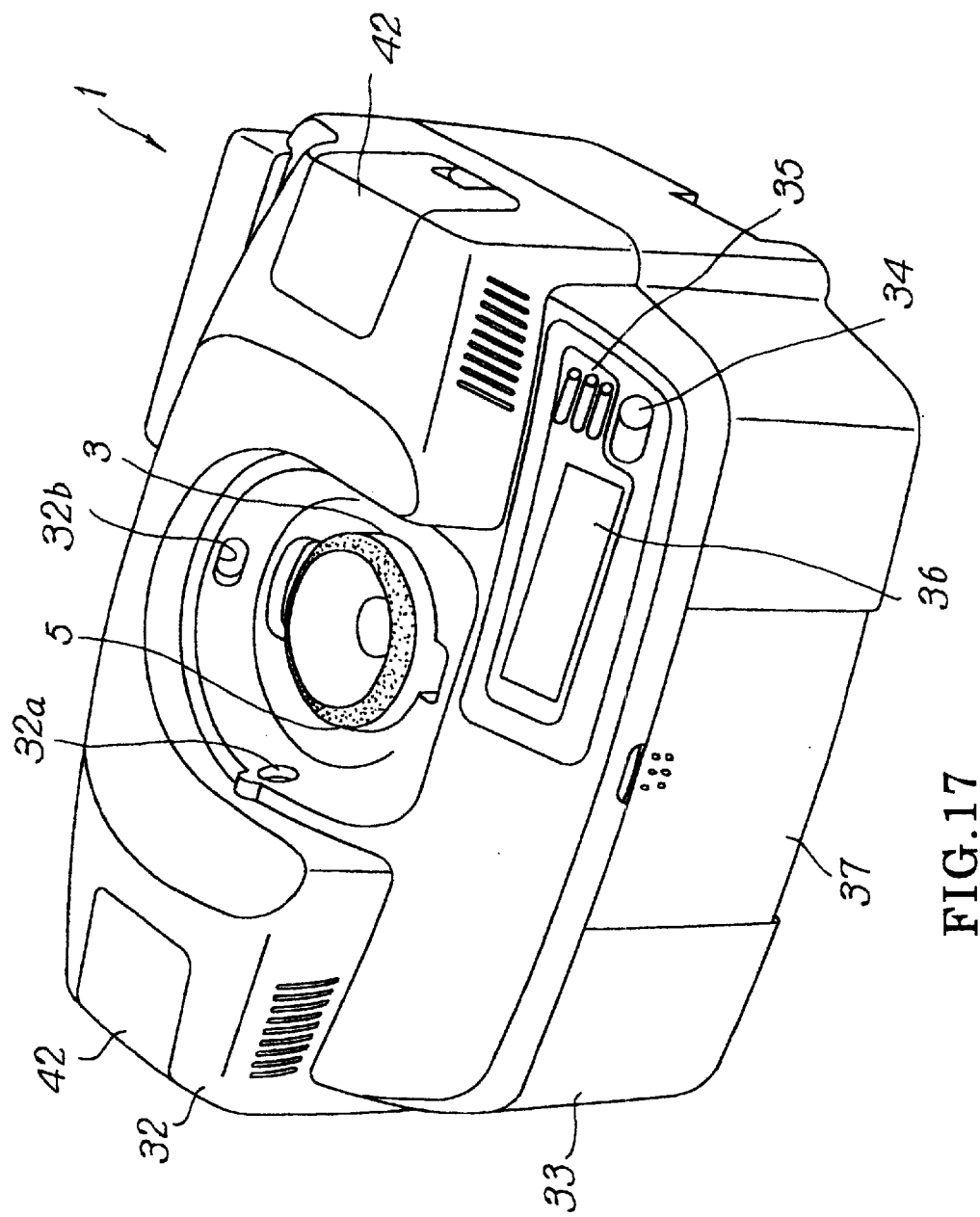
FIG. 17 is an external perspective view of an apparatus for evaluating the inner quality of vegetables and fruits according to a further embodiment of the present invention.
Figure 18:
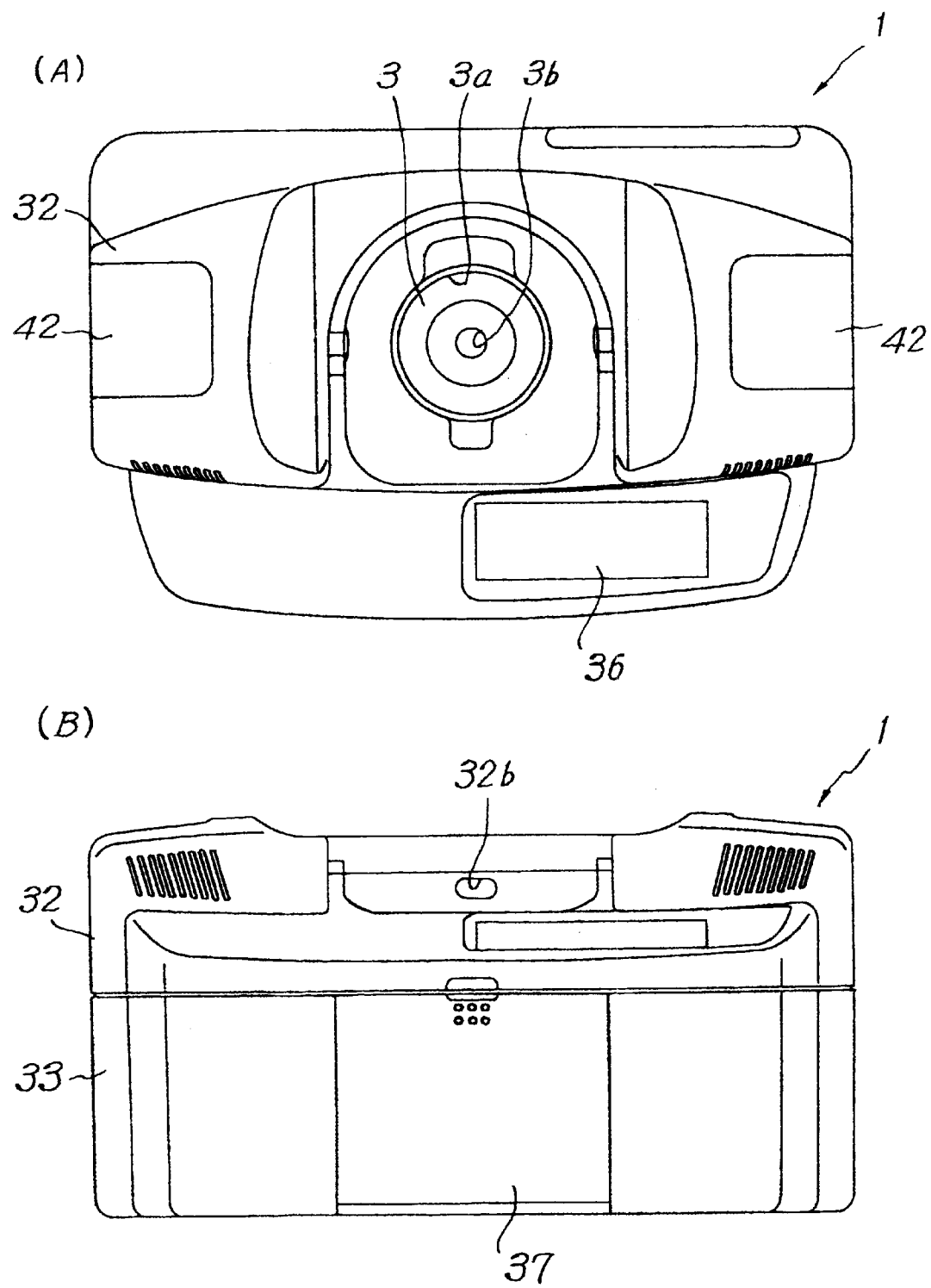
FIGS. 18(A) and 18(B) show the external appearance of an apparatus for evaluating the inner quality of vegetables and fruits according to a further embodiment of the present invention, (A) being a plan view, (B) being a front view.
Figure 19:
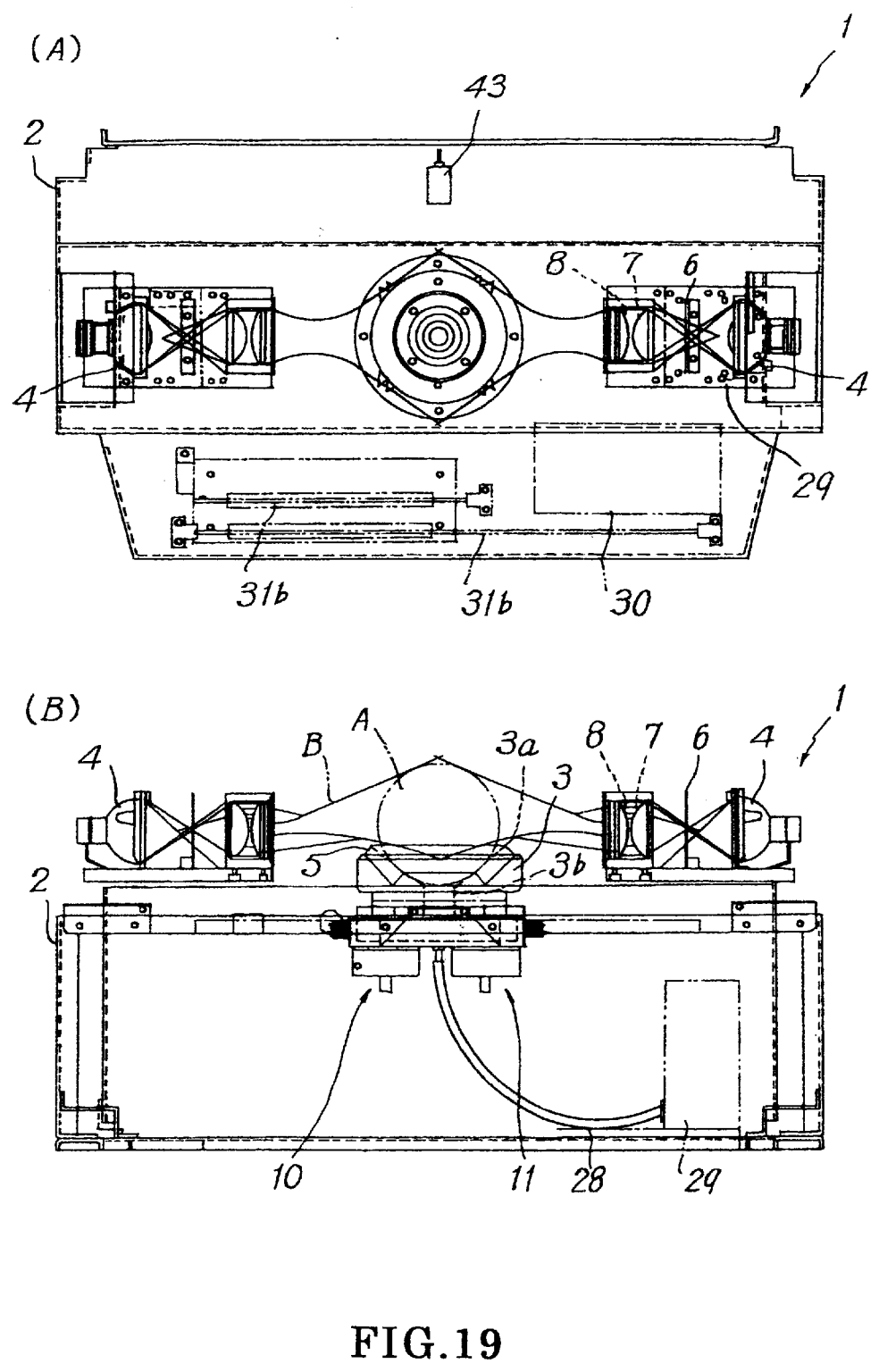

An apparatus for evaluating the inner quality of vegetables and fruits 101 according to another embodiment of the present invention is constituted similarly to the aforementioned apparatus for evaluating the inner quality of vegetables and fruits 1. However, as shown in FIG. 19, at the rear of an apparatus for evaluating the inner quality of vegetables and fruits 17 is arranged a position sensor 43 comprising a photo sensor, and as shown in FIGS. 17 and 18, a detecting passage hole 32b is formed in the rear inner surface of a central cave-in portion of the upper cover 32.

Figure 20:
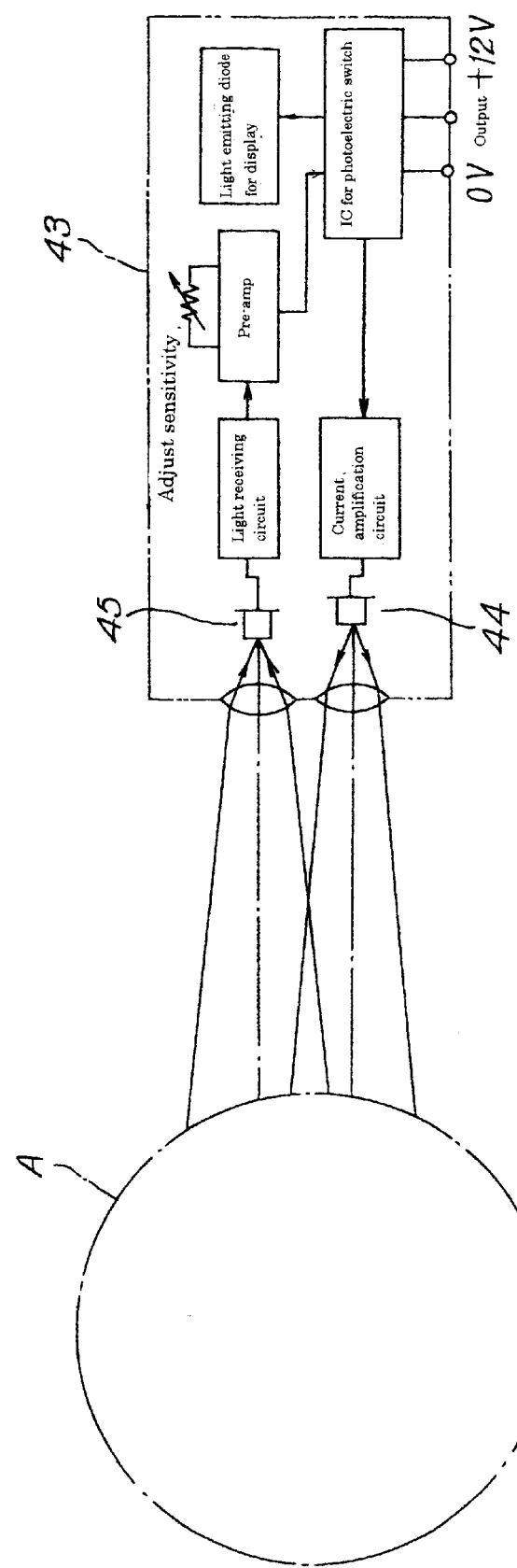
FIG. 20 is a position sensor circuit constitutional view of an apparatus for evaluating the inner quality of vegetables and fruits according to another embodiment of the present invention.

The position sensor 43 is constituted as shown in FIG. 20. Infrared ray radiated from a light emitting diode 44 is projected in the upper vicinity of the place bed 3 through the detecting passage hole 32b, and a reflecting light is received by a photo transistor 45 to thereby enable detecting whether or not the vegetables and fruits A are placed on the place bed 3.

The detecting passage hole 32b is formed at a position that a projecting light path of infrared ray is not cut off in the rear side of the correcting cover 24, and the detection distance of the position sensor 43 is set to a considerably short distance from the front side of the correcting cover 24.

Figure 11:
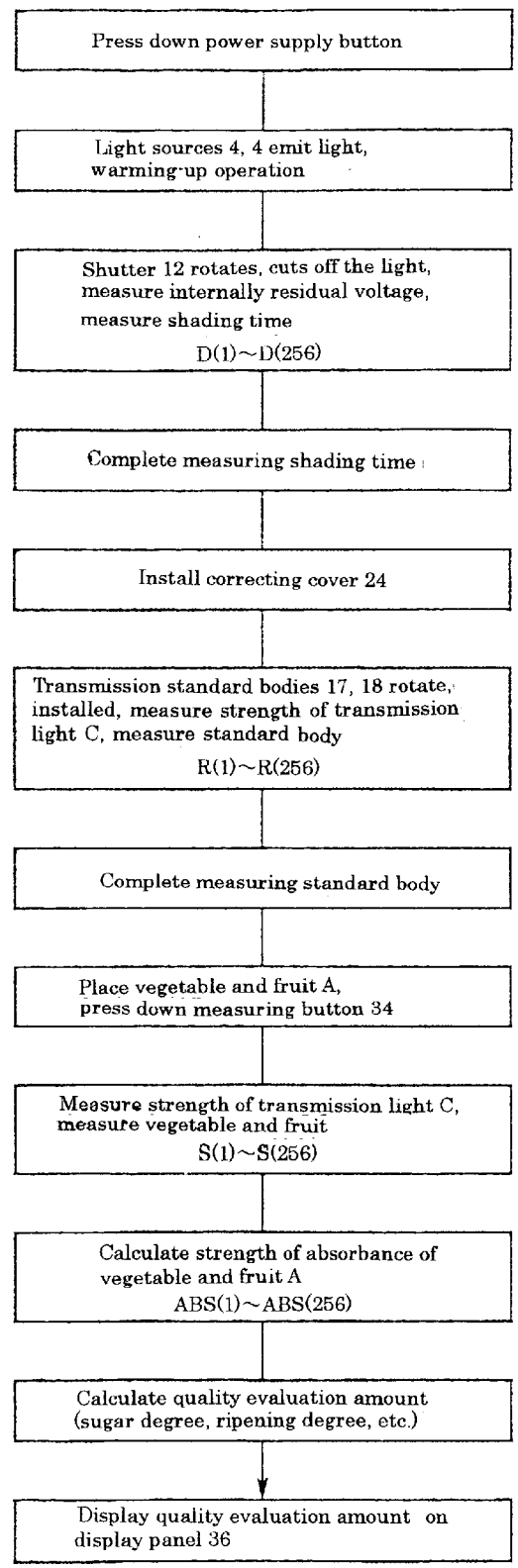
FIG. 11 is a process (step) view showing the quality evaluating procedure of the apparatus for evaluating the inner quality of vegetables and fruits of the present invention.
Figure 21:
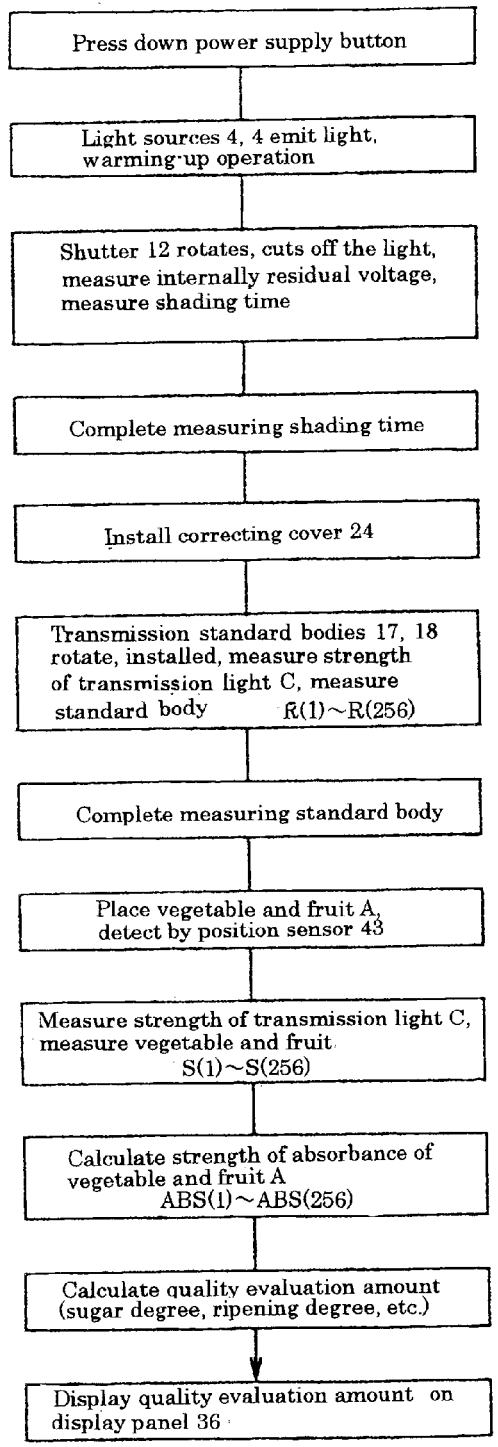
FIG. 21 is a process (step) view showing the quality evaluating procedure in a case that set to the automatic measuring mode in the apparatus for evaluating the inner quality of vegetables and fruits according to the present invention.

Next, the operation and the effect of the apparatus for evaluating the inner quality of vegetables and fruits 101 according to the present invention will be described with reference to FIGS. 11 and 21 along with the using method.

First, when a power supply button (not shown) disposed on the back of the apparatus for evaluating the inner quality of vegetables and fruits 101 is pressed down to turn on the power supply, the power supply display lamp 35a lights, the light sources 4, 4 start to emit light, and the warming-up operating state is displayed on the display panel 36.

The warming-up operating state continues and when the temperature sensor 9 detects that the temperature around the light sources 4, 4 reaches the fixed temperature, the termination of the warming-up operation is displayed on the display panel 36.

Figure 12:
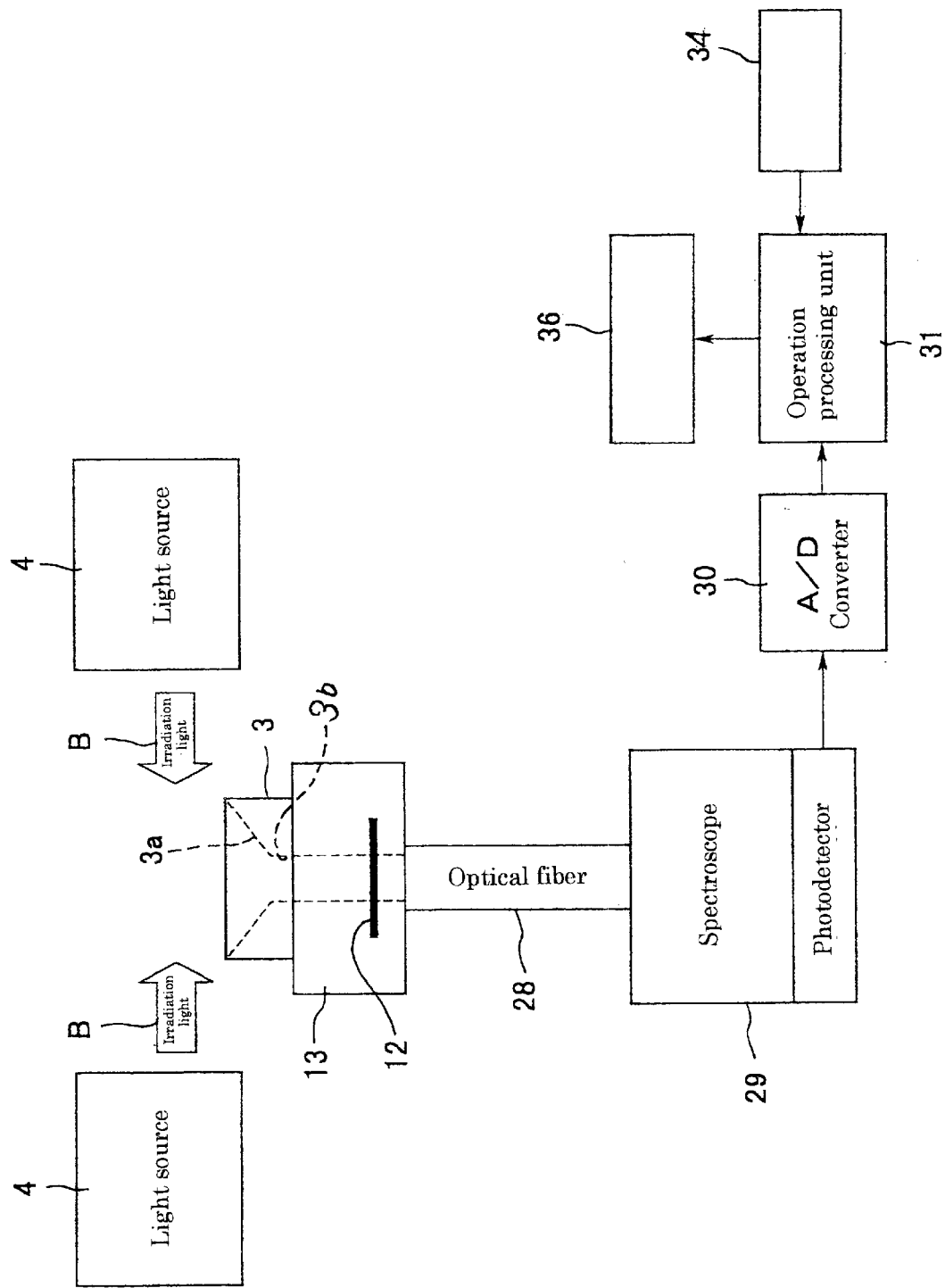
FIG. 12 is a schematic explanatory view showing the shading time measuring state in the apparatus for evaluating the inner quality of vegetables and fruits of the present invention.

Then, the shutter drive device 13 is automatically actuated, the shutter 12 is rotated, and as shown in FIG. 12, the external light including the irradiation light B from the light sources 4, 4 is cut off, and the shading measuring state is displayed on the display panel 36.

In the shading measuring state, the internally residual voltage in the optical fiber 28, the spectra/detection unit 29 or the like is measured by the spectra/detection unit 29. Here, since the frequency area is divided into 256, internally residual voltage data D (1)~D (256) are to be obtained.

When the shading time measurement is completed, the completion of the shading time measurement is displayed on the display panel 36, and the instructions for installing the correcting cover 24 is displayed.

Figure 13:
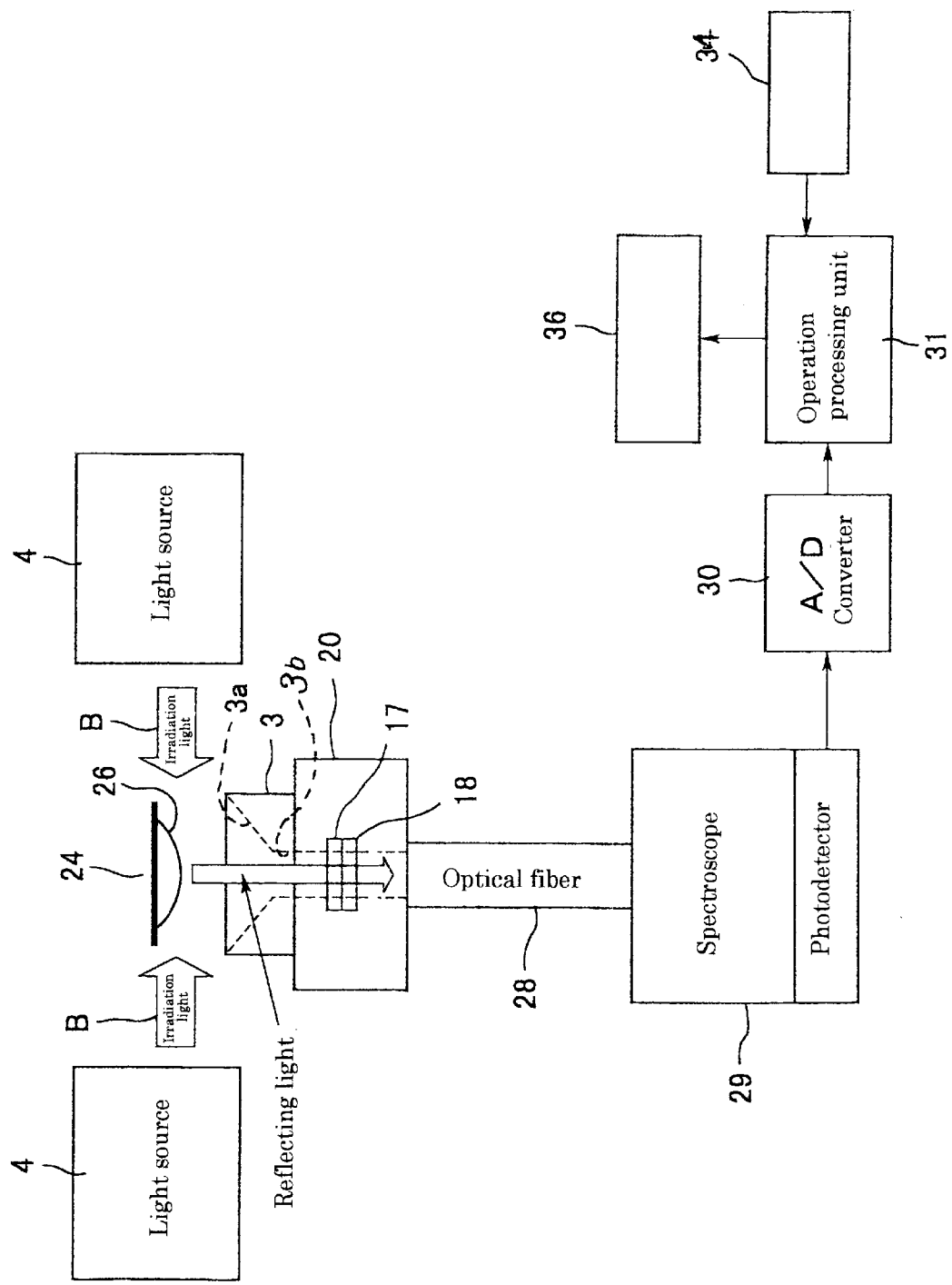
FIG. 13 is a schematic explanatory view showing the standard body measuring state in the apparatus for evaluating the inner quality of vegetables and fruits of the present invention.

When an operator installs the correcting cover 24, which was detected by a position sensor (not shown), the transmission standard body drive device 20 is automatically actuated to rotate the transmission standard bodies 17, 18, and as shown in FIG. 13, the irradiation light B from the light sources 4, 4 is reflected by the reflecting standard body 26, passes through the transmission light detecting hole 3b, passes through the transmission standard bodies 17, 18 into the transmission light C, which passes through the optical fiber 28 and is guided to the spectra/detection unit 29, and the standard body measuring state is displayed on the display panel 36.

In the standard body measuring state, the transmission light C is divided into a number of frequency areas by the spectra/detection unit 29, and the optical strength of every frequency area is measured. Here, since the frequency area is divided into 256, optical strength data R (1)~R (256) are to be obtained.

When the standard body measurement is completed, the measurement ready completion display lamp 35c is lighted to display the completion of the standard body measurement on the display panel 36, and display the vegetables and fruits measurable state.

In a case where the automatic measuring mode is selected in advance by the menu button 39a of the environment setting button 39 of the operating panel 37, when an operator revolts against the correcting cover 24 to place the vegetables and fruits A on the place bed 3, the position sensor 43 detects that the vegetables and fruits A are placed on the place bed 3, and the measurement automatically starts.

As shown in FIG. 14, the irradiation light B from the light sources 4, 4 transmits through the vegetables and fruits A into the transmission light C, which passes through the transmission light detecting hole 3b and the optical fiber 28, is guided to the spectra/detection unit 29, and the vegetables and fruits measuring state is displayed on the display panel 36.

In the vegetables and fruits measuring state, the transmission light C is divided into a number of frequency areas by the spectra/detection unit 29, and the optical strength of every frequency area is measured. Here, since the frequency area is divided into 256, optical strength data S (1)~S (256) are to be obtained.

On the other hand, in a case where the manual measuring mode is selected in advance by the menu button 39a of the environment setting button 39 of the operating panel 37, an operator revolts against the correcting cover 24 to place the vegetables and fruits A on the place bed 3, and presses down the measuring button 34, then the measurement is started.

When the vegetables and fruits measurement is completed, the absorbance of every frequency area caused by the vegetables and fruits A is calculated as the ABS (1)~ABS (256) from the optical strength data S (1)~S (256), R (1)~R (256), and the internally residual voltage data D (1)~D (256) by the operation processing unit 31.

The quality evaluation amounts such as the sugar degree, the ripening degree, the honey amount, and the degree of changing into brown are calculated or decided from the absorbance data ABS (1)~ABS (256), and are displayed on the display panel 36, as shown in FIG. 15, by letters or numerical values along with the kind and the breed of vegetables and fruits.

As the means for detecting whether or not the vegetables and fruits A are placed on the place bed 3, a weight sensor may be employed in place of the position sensor 43.

Figure 22:
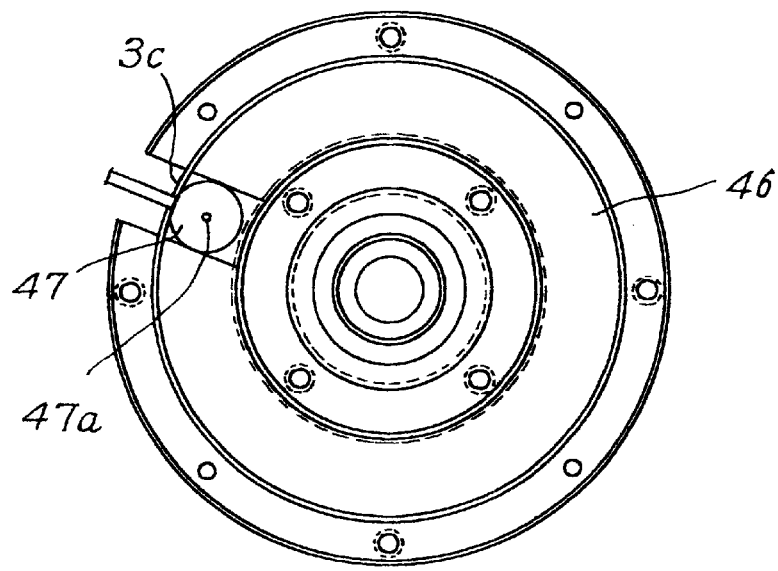
FIGS. 22(A) and 22(B) show the neighborhood of the place bed of the apparatus for evaluating the inner quality of vegetables and fruits in a case where a weight sensor is employed as detection means, (A) being a plan view, (B) being a front view.
Figure 22:
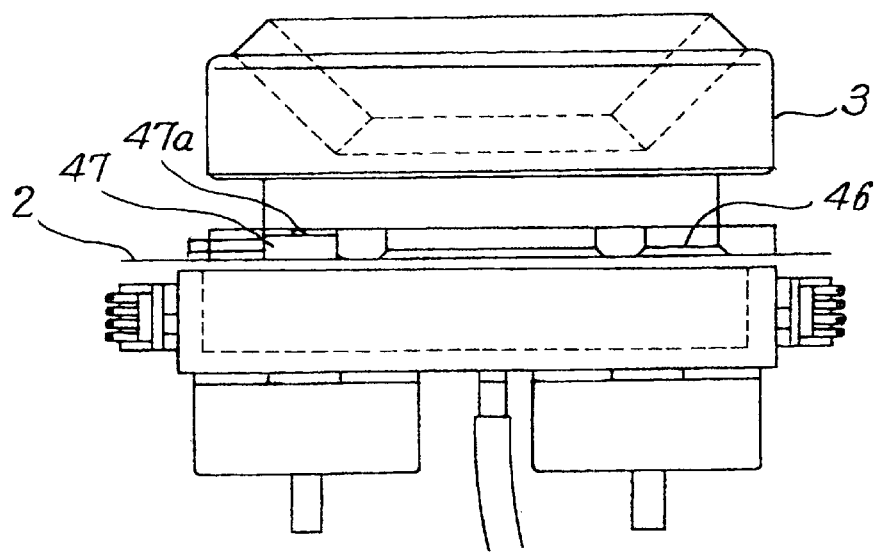

In a case where the weight sensor is employed, for example, as shown in FIG. 22, an elastic member 46 such as soft rubber, cellular plastic or the like is interposed between the bottom surface of the place bed 3 and the upper surface of the casing 2, a weight sensor 47 comprising a load cell is disposed at a cut portion 3c formed in the lower end of the place bed 3, and the bottom surface of the place bed 3 is placed in contact with a load receiving shaft 47a of the weight sensor 47.

According to the constitution as described above, a load applied to the load receiving shaft 47a is detected, whereby whether or not the vegetables and fruits A are placed on the place bed 3 can be detected.

As the means for detecting whether or not the vegetables and fruits A are placed on the place bed 3, particularly, any sensor may not be used.

Figure 23:
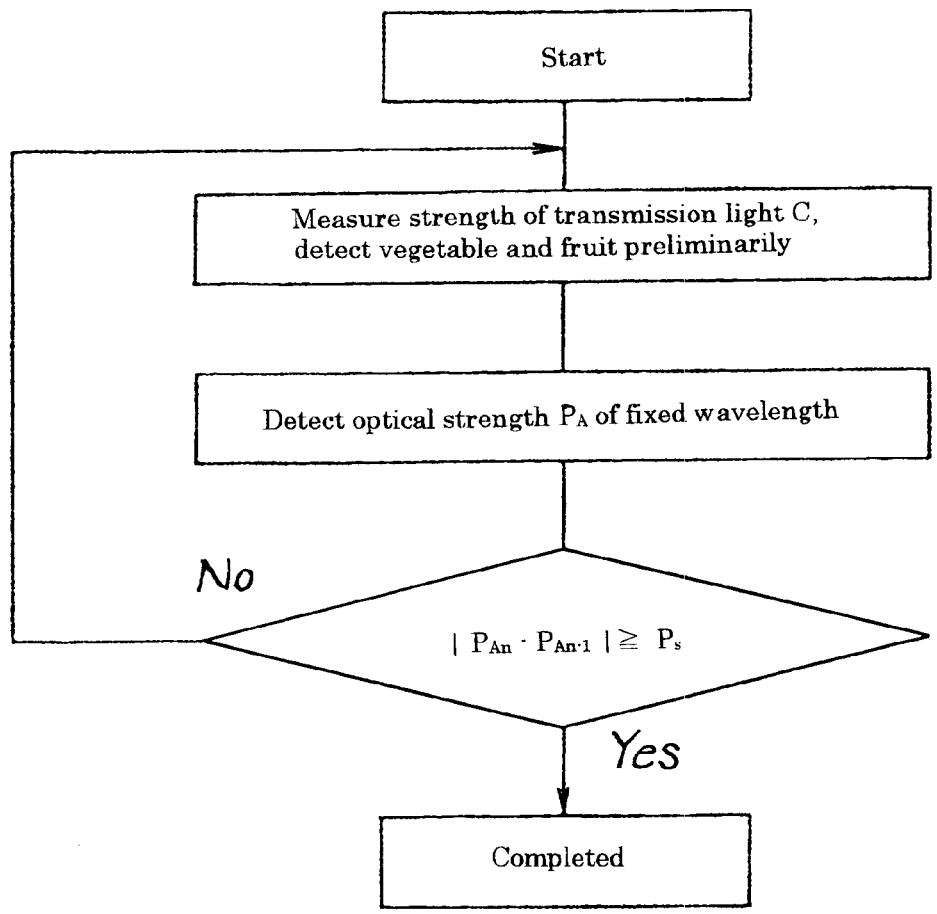
FIG. 23 is a process (step) view showing the procedure for detecting whether or not vegetables and fruits are placed in a case where the optical strength is preliminarily measured as detection means.
Figure 24:
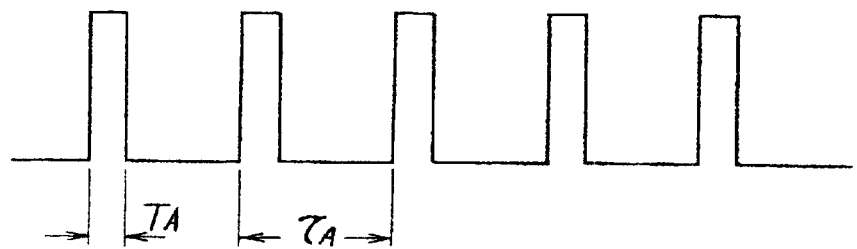
FIG. 24 is an explanatory view showing the measuring time, the period and the measured result in a case where the optical strength is preliminarily measured as detection means.
Figure 24:
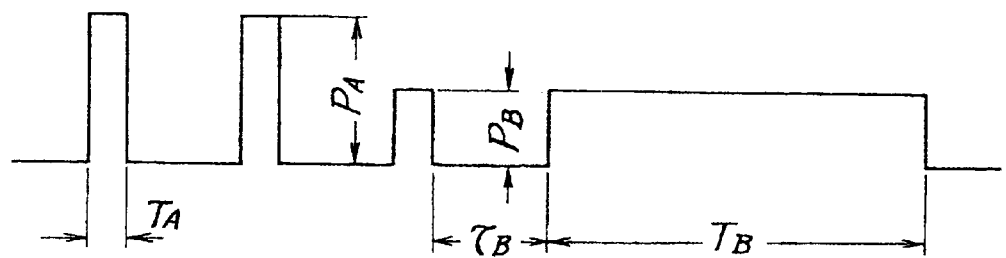

At the time of the vegetables and fruits measurable state, as shown in FIGS. 23 and 24, the strength of the transmission light C may be measured preliminarily in a relatively short time $T_A$ every fixed period $\tau_A$. Here, the time $T_A$ is about 10 msec, and the period $\tau_A$ is about 10 msec~1 sec.

In the preliminary measurement, the optical strength $P_A$ of the fixed wavelength is a detection value. Normally, the wavelength in the range of 700~850 nm indicative of the most efficient optical strength in the detection is selected.

According to such a method as described, at the time of the vegetables and fruits measurable state, as shown in FIGS. 19 and 20, the strength of the transmission light C is measured preliminarily to detect the optical strength $P_A$ of the fixed wavelength, and the optical strength $P_{An}$ of this time is compared with the optical strength $P_{An-1}$ of previous time.

Since the optical strength $P_B$ when the vegetables and fruits A are placed should be considerably smaller than the optical strength $P_A$ when the vegetables and fruits A are not placed, it is possible to detect whether or not the vegetables and fruits A are placed on the place bed depending on whether or not $|P_{An} \cdot P_{An-1}|$ is in excess of a fixed value $P_s$.

In a case where $|P_{An} \cdot P_{An-1}|$ is not more than the fixed value $P_s$, the preliminary measurement is repeated, and in a case where $|P_{An} \cdot P_{An-1}|$ is not less than the fixed value $P_s$, the preliminary measurement is completed, and the real measurement of the inner quality is automatically executed.

The real measurement is started when the preliminary measurement is completed and after the time $\tau_B$, and the measuring time $T_B$ is suitably set within the range of 100 msec~1 sec.

The apparatus for evaluating the inner quality of vegetables and fruits 101 according to the present invention is constituted such that the place bed, the light sources, the spectra/detection unit, the operation processing unit, the operating button, the display panel or the like are enveloped compactly, can be installed on the table, and is portable, thus being small and inexpensive, and can be easily introduced even for small enterprisers. Further, the installation place can be changed easily, which is very convenient.

Further, if design is made so that whether or not the vegetables and fruits are placed on the place bed is detected by suitable detection means, and the measurement is automatically started, an operator is able to make measurement easily, and the measuring time can be shortened without carrying out troublesome operation.

Next, a description will be made of a warming-up operating method in the apparatus for evaluating the inner quality of vegetables and fruits in which the apparatus is subject to the warming-up operation only for a period of time as necessary whereby the waiting time which is more than as needed or entirely wasteful is omitted, while sufficiently securing the accuracy of measurement and evaluation, and the enhancement of working efficiency and energy saving can be realized.

Figure 25:
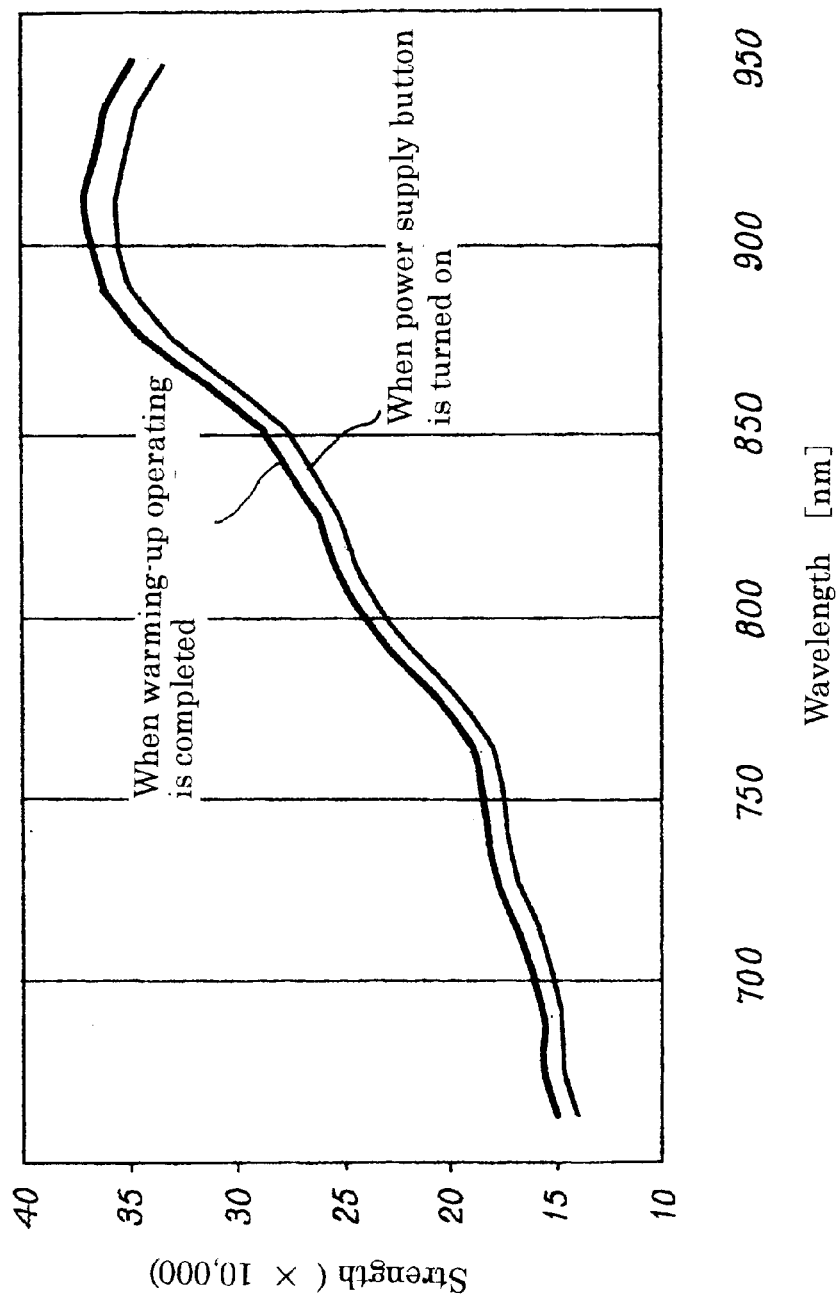
FIG. 25 is a view showing the change in a lapse of time of a spectra of a light source after power is turned on in the apparatus for evaluating the inner quality of vegetables and fruits.
Figure 26:
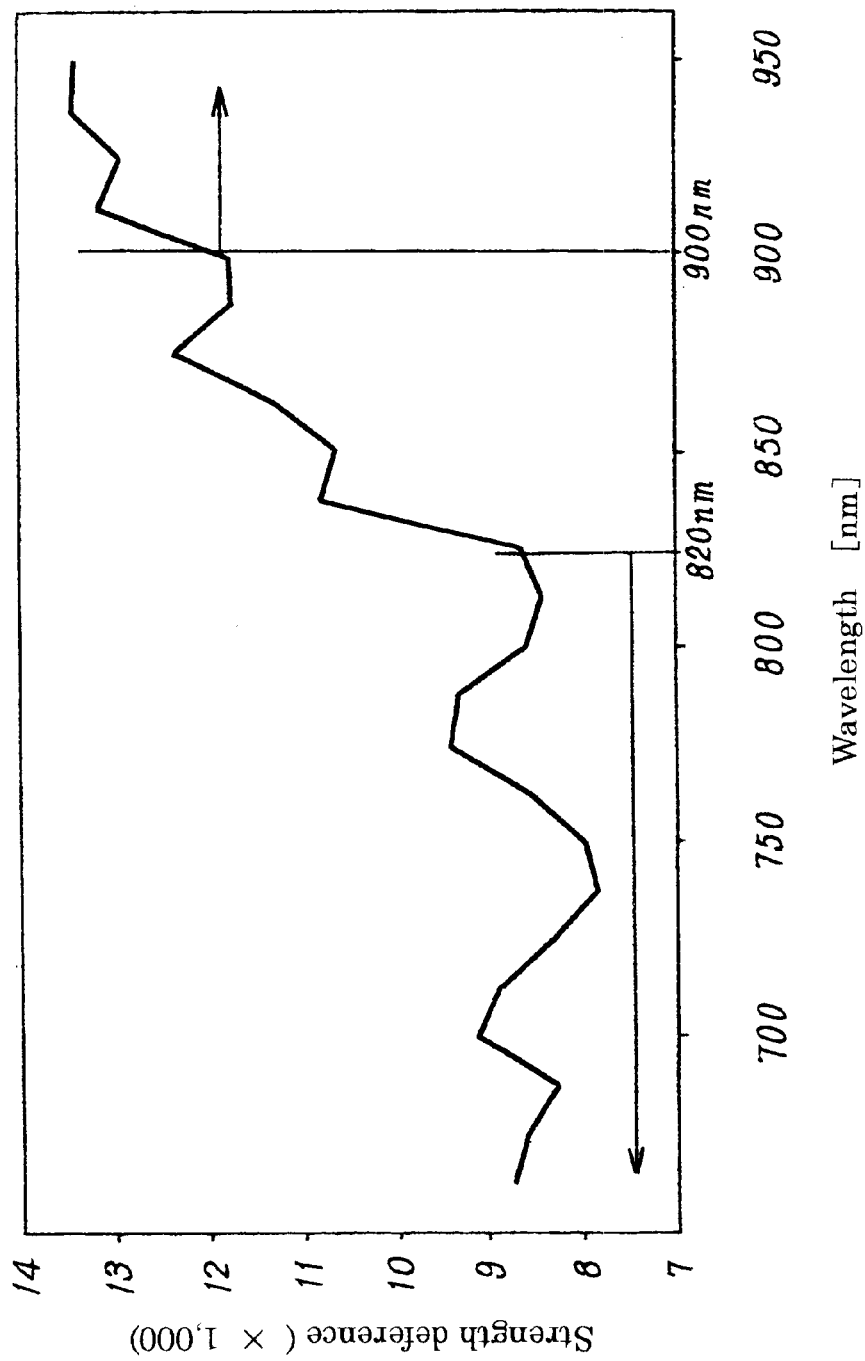
FIG. 26 is a view showing the strength difference of a spectra of a light source when the power is turned on and when the warming-up operation is terminated.

FIG. 25 is a view showing a change of a lapse of time of a spectra of a light source after a power supply has been turned on in the apparatus for evaluating the inner quality of vegetables and fruits, and FIG. 26 is a view showing a strength difference of a light source spectra between when power is turned on and when warming-up operation is completed.

From these drawings, there can be seen a large difference in strength difference between light of not more than 820 of wavelength and light of not less than 900 of wavelength. Observing the strength ratio or strength difference between two lights in two wavelength areas, it is possible to decide the warming-up operation completion time.

Figure 27:
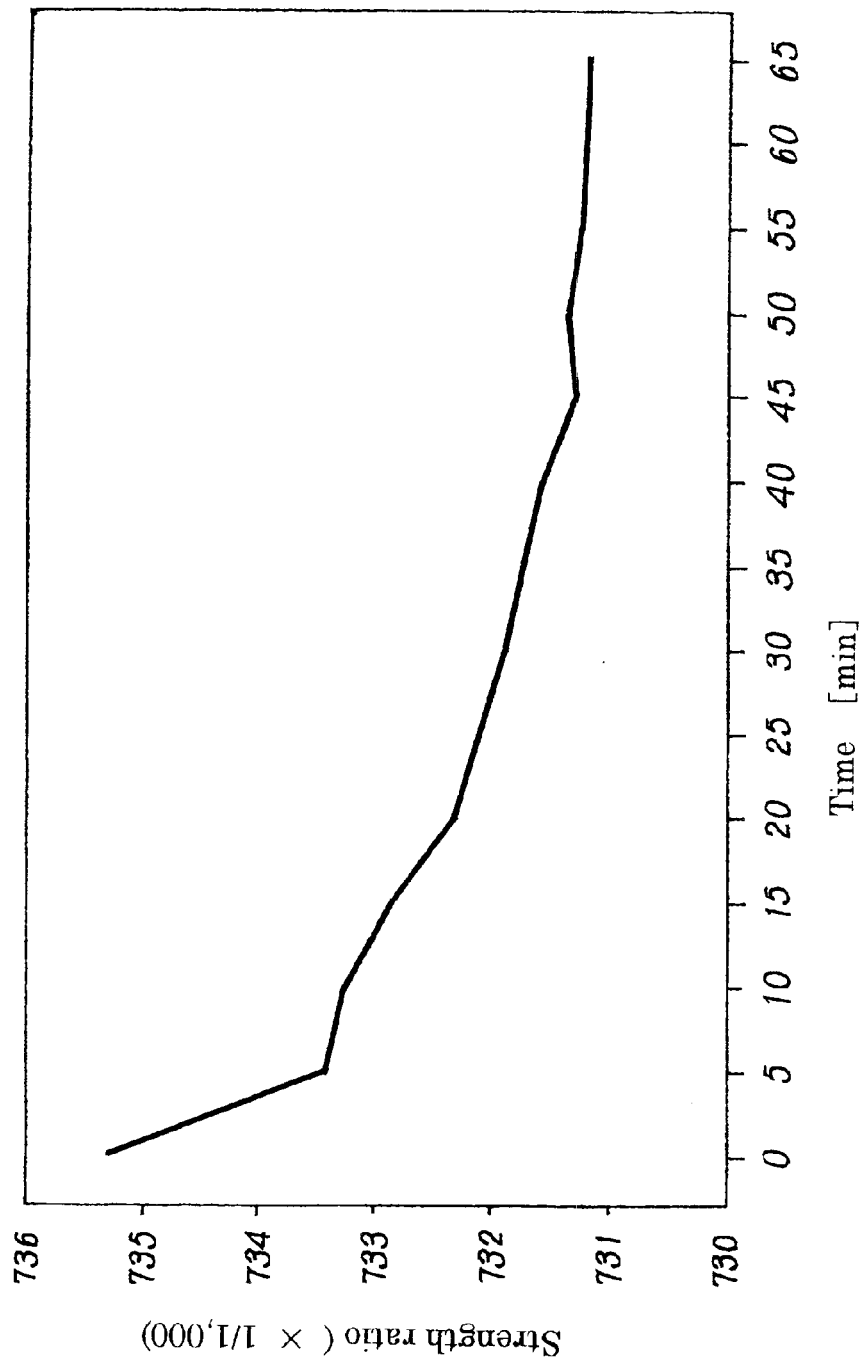
FIG. 27 is a view showing the change by way of a lapse of time of the strength ratio in a case where light of wavelengths of 800 nm and 930 nm is selected.
Figure 28:
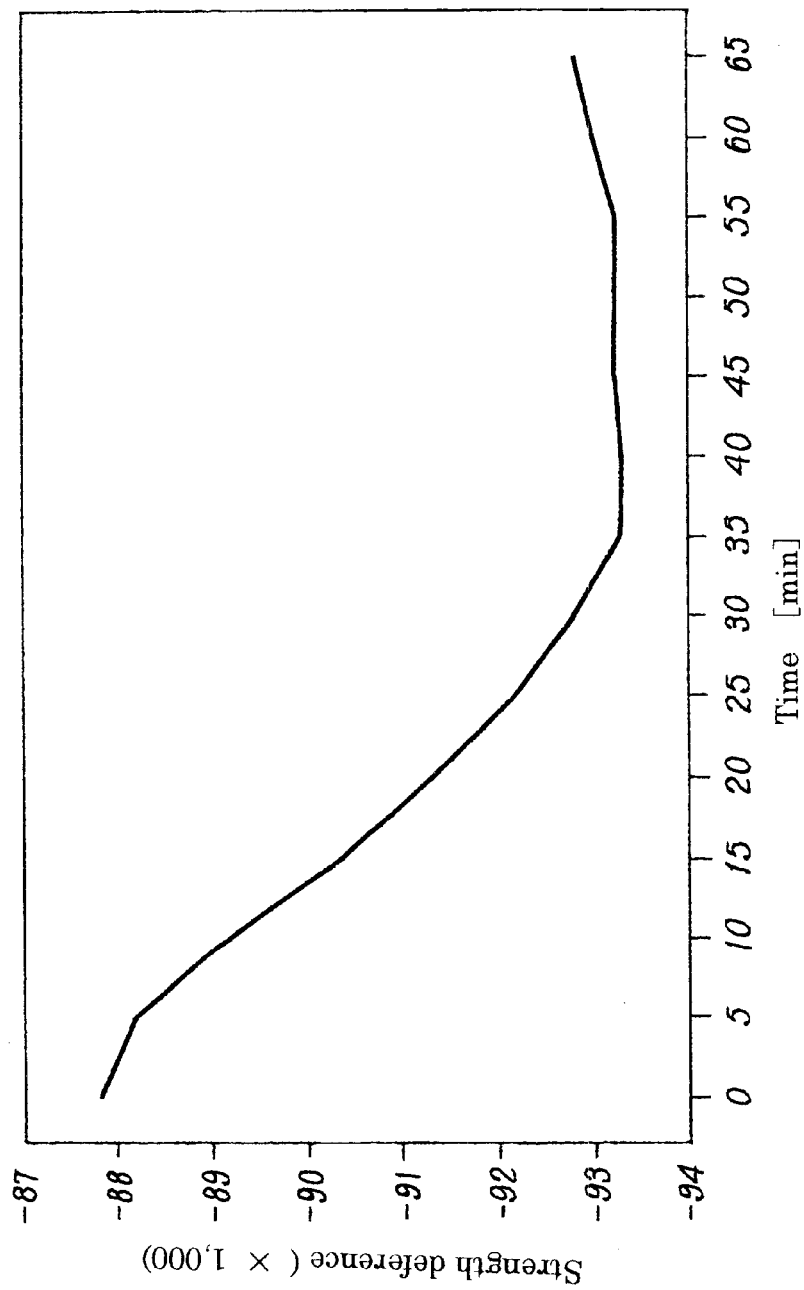
FIG. 28 is a view showing the change by way of a lapse of time of the strength difference in a case where light of wavelengths of 800 nm and 930 nm is selected.

FIG. 27 and FIG. 28 show the change of a lapse of time of the strength ratio in a case where lights of wavelength 800 nm and 930 nm are selected, and the change of a lapse of time of the strength difference, respectively.

In FIG. 27, the strength ratio is stabilized at not more than 0.7315, and in FIG. 28, the strength difference is stabilized at not more than 93000, whereby the completion time of the warming-up operation can be decided.

Figure 29:
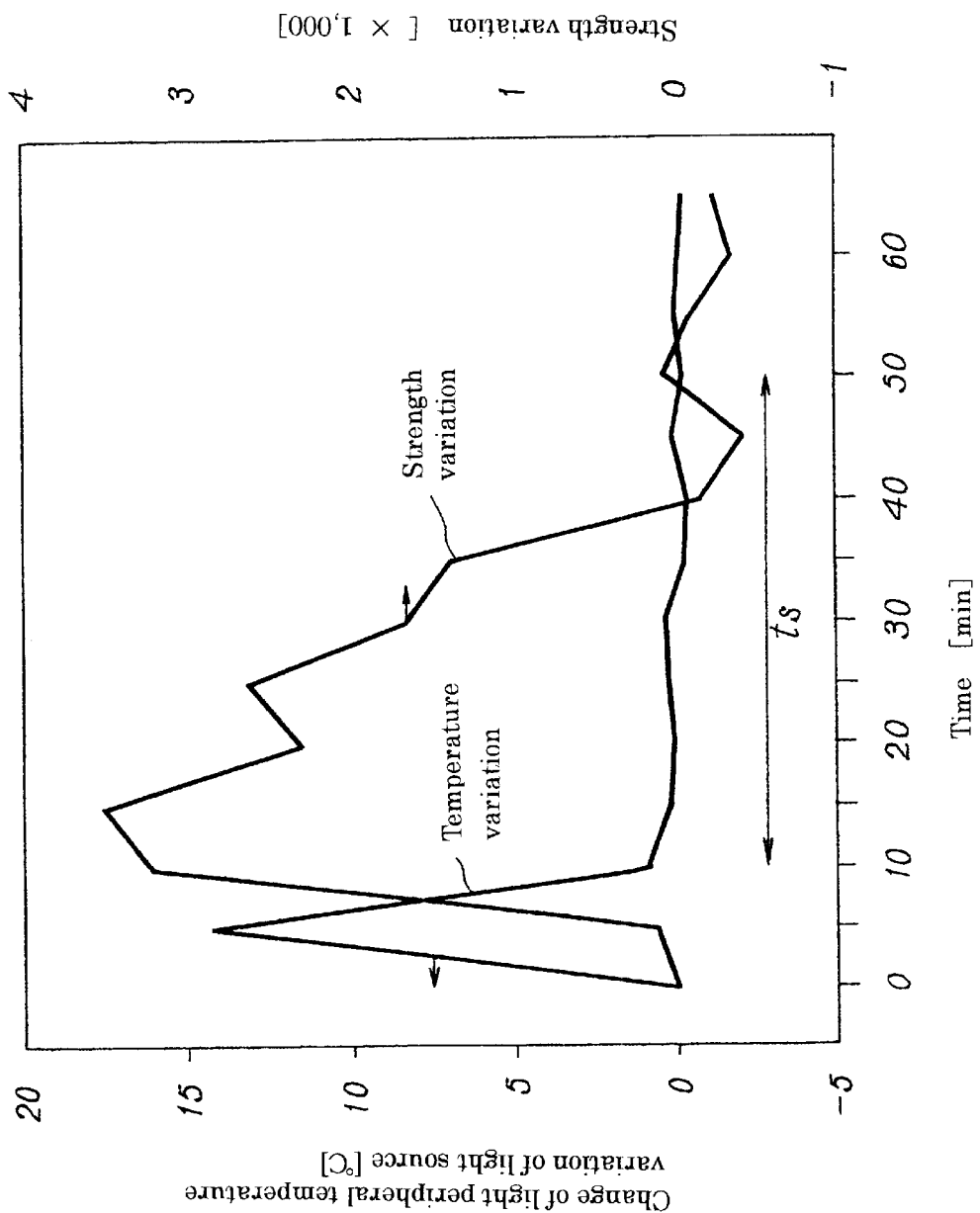
FIG. 29 is a view showing the change by way of a lapse of time of the variation of peripheral temperature of a light source and the strength variation of light of wavelength of 800 nm in the apparatus for evaluating the inner quality of vegetables and fruits.

FIG. 29 is a view showing the change of a lapse of time of the peripheral temperature variation of a light source and the strength variation of light of wavelength 800 nm in the apparatus for evaluating the inner quality of vegetables and fruits.

It is understood from the figure that the peripheral temperature is first stabilized after the power is turned on, and the light strength is stabilized after the passage of a fixed period of time. It is also understood that the time till the peripheral temperature is stabilized differs depending upon the environment temperature or the like, and the time ts required from the stabilization of the peripheral temperature to the stabilization of the strength of light is generally constant.

Therefore, the peripheral temperature is measured in a manner of a lapse of time and stabilized, after which the fixed time ts is added whereby the completion time of the warming-up operation can be decided.

Figure 30:
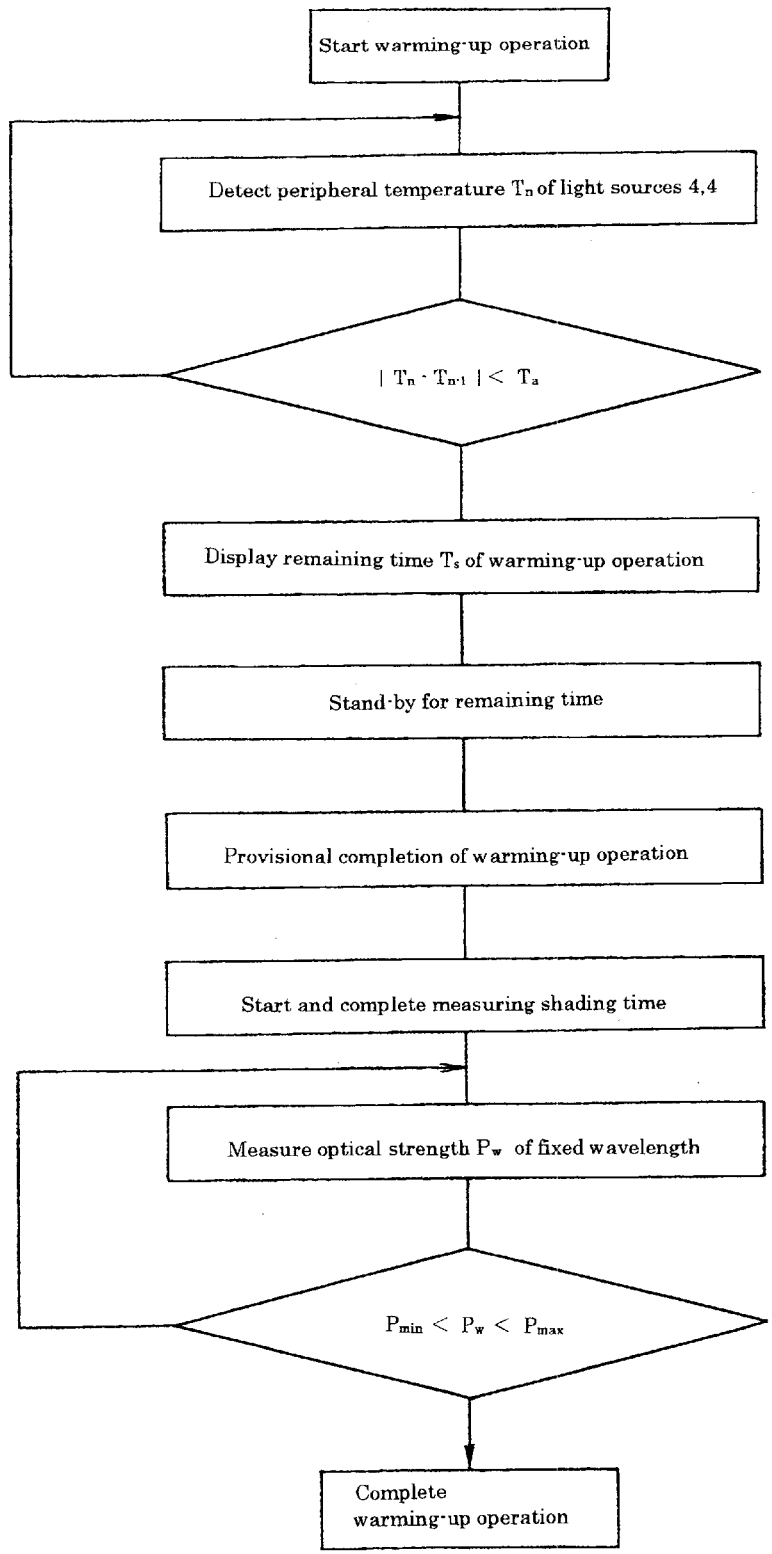
FIG. 30 is a process (step) view showing the method for warming-up operating in the apparatus for evaluating the inner quality of vegetables and fruits.

Next, the warming-up operating method for detecting the peripheral temperature of the light sources 4, 4 in a manner of a lapse of time to decide the completion time of the warming-up operation will be described along with the operation, the effect and the using method of the apparatus for evaluating the inner quality of vegetables and fruits 1 with reference to FIGS. 11 and 30.

First, when a power supply button (not shown) disposed on the back of the apparatus for evaluating the inner quality of vegetables and fruits 1 is pressed down to turn on the power supply, the power supply display lamp 35a lights so that the light sources 4, 4 start to emit light, and the warming-up operating state is displayed on the display panel 36.

When the warming-up operation is started (Step 1), the temperature sensor 9 detects the peripheral temperature of the light source 4 every fixed period $\tau_1$, and its detected value $T_n$ is taken into the operation processing unit 31 (Step 2).

The operation processing unit 31 decides whether or not the absolute value of a difference between the detected value $T_n$ of this time and the detected value $T_{(n-1)}$ of previous time is smaller than the allowable temperature variation width $T_a$ (Step 3). If the decision is No, the peripheral temperature of the light sources 4, 4 is not stabilized, and the steps 2 and 3 are repeated till the decision becomes Yes.

When in Step 3, the decision is Yes, since the remaining time of the warming-up operation after that time is given by ts, ts is displayed as the remaining time of the warming-up operation on the display panel 36 (Step 4).

When the warming-up operation is further executed (Step 5) and the time ts has passed, the completion of the warming-up operation for the time being is displayed on the display panel 36 (Step 6), and subsequently, the process for the preparation of the measurement of the inner quality of vegetables and fruits is executed (Step 7).

That is, the shutter drive device 13 is automatically actuated so that the shutter 12 is rotated, and as shown in FIG. 12, the external light including the irradiation light B from the light sources 4, 4 is cut off, and the shading time measuring state is displayed on the display panel 36.

In the shading time measuring state, the internal residual voltage in the optical fiber 28, the spectra/detection unit 29 or the like is measured by the spectra/detection unit 29. Here, since the frequency area is divided into 256, the internal residual voltage data D (1)~D (256) are to be obtained.

When the shading time measurement is completed, the completion of the shading time measurement is displayed on the display panel 36 to display the instructions for installing the correcting cover 24.

When the operator installs the correcting cover 24 and the position sensor (not shown) detects it, the transmission standard drive device 20 is automatically actuated so that the transmission standard bodies 17, 18 are rotated, and as shown in FIG. 13, the irradiation light B from the light sources 4, 4 is reflected by the reflecting standard body 26, passes through the transmission light detecting hole 3b and passes through the transmission standard bodies 17, 18 into the transmission light C, which passes through the optical fiber 28 and is guided to the spectra/detection unit 29, and the standard body measuring state is displayed on the display panel 36.

In the standard body measuring state, the transmission light C is divided into a number of frequency areas by the spectra/detection unit 29, and the optical strength of every frequency area is measured. Here, since the frequency area is divided into 256, the optical strength data R (1)~R (256) are to be obtained.

At the time of the standard body measurement, whether or not the spectra of the light source is stabilized is confirmed. That is, the detection value Pw of the optical strength of the fixed wavelength is taken into the operation processing unit 31 (Step 8), and the detection value $P_w$ of the optical strength is compared with the allowable minimum value $P_{min}$ and the allowable maximum value $P_{max}$ (Step 9).

If the detection value $P_W$ of the optical strength is within the allowable range of the optical strength, the warming-up operation is finally completed (Step 10), and if outside the allowable range, the steps 8 and 9 are repeated at a fixed period $\tau_2$ till it is within the allowable range.

When the warming-up operation is finally completed, and the standard body measurement is completed, the measurement preparation completion display lamp 35c lights, and the final completion of the warming-up operation is displayed on the display panel 36, and the vegetables and fruits measurable state is displayed.

When the operator revolts against the correcting cover 24, places the vegetables and fruits on the place bed 3 and presses down the measuring button 34, as shown in FIG. 14, the irradiation light B from the light sources 4, 4 transmits through the vegetables and fruits A into the transmission light C, which passes through the transmission light detecting hole 3b and the optical fiber 28 and is guided to the spectra/detection unit 29, and the vegetables and fruits measuring state is displayed on the display panel 36.

In the vegetables and fruits measuring state, the transmission light C is divided into a number of frequency areas by the spectra/detection unit 29, and the optical strength of every frequency area is measured. Here, since the frequency area is divided into 256, the optical strength data S (1)~S (256) are to be obtained.

When the vegetables and fruits measurement is completed, the absorbance of every frequency area caused by the vegetables and fruits A is calculated as the ABS (1)~ABS (256) from the optical strength data S (1)~S (256), R (1)~R (256), and the internally residual voltage data D (1)~D (256) by the operation processing unit 31.

The quality evaluation amounts such as the sugar degree, the ripening degree, the honey amount, and the degree of changing into brown are calculated or decided from the absorbance data ABS (1)~ABS (256), and are displayed on the display panel 36, as shown in FIG. 15, by letters or numerical values along with the kind and the breed of vegetables and fruits.

Figure 31:
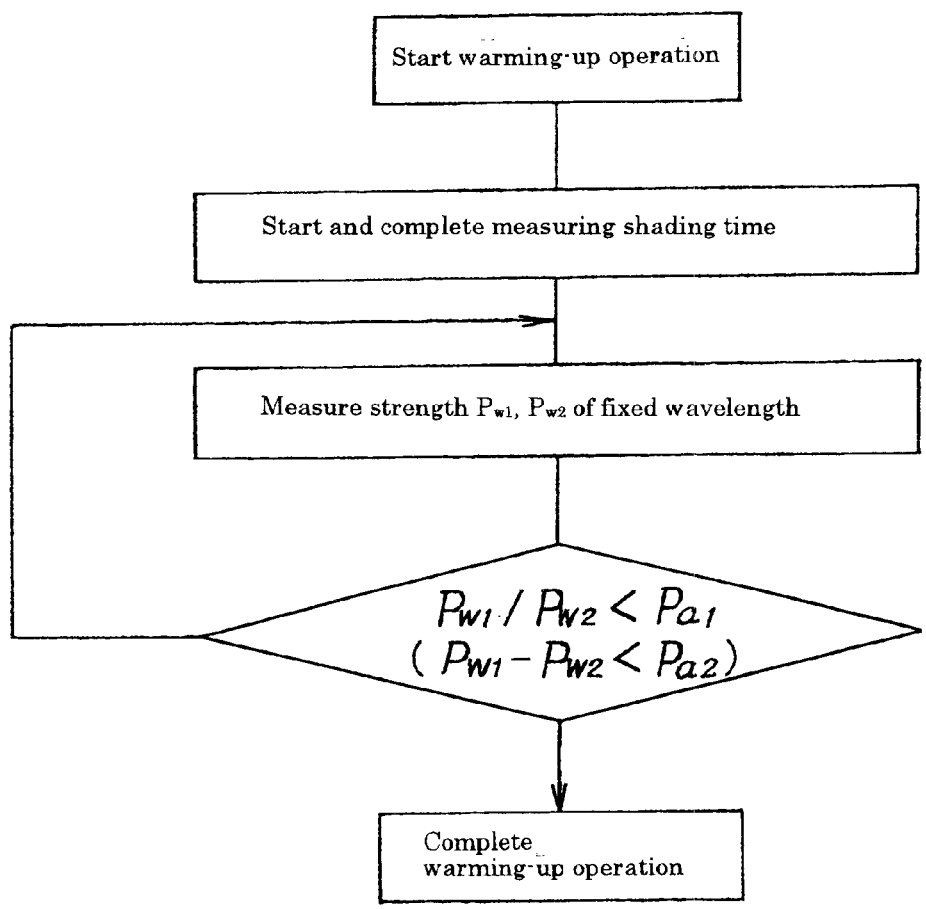
FIG. 31 is a process (step) view showing the method for warming-up operating in the apparatus for evaluating the inner quality of vegetables and fruits.

Next, the warming-up operating method for detecting the strength of the light in the fixed wavelength of spectra of the light source in a manner of a lapse of time to decide the completion time of the warming-up operation will be described along with the operation, the effect and the using method of the apparatus for evaluating the inner quality of vegetables and fruits 1 with reference to FIGS. 11 and 31.

First, when a power supply button (not shown) disposed on the back of the apparatus for evaluating the inner quality of vegetables and fruits 1 is pressed down to turn on the power supply, the power supply display lamp 35a lights so that the light sources 4, 4 start to emit light, and the warming-up operating state is displayed on the display panel 36.

When the warming-up operation is started (Step 1), the step for the measurement preparation of the inner quality of vegetables and fruits is executed immediately (Step 2).

That is, the shutter drive device 13 is automatically actuated, and the shutter 12 is rotated, and as shown in FIG. 12, the external light including the irradiation light B from the light sources 4, 4 is cut off, and the shading time measuring state is displayed on the display panel 36.

In the shading time measuring state, the internal residual voltage in the optical fiber 28, the spectra/detection unit 29 or the like is measured by the spectra/detection unit 29. Here, since the frequency area is divided into 256, the internal residual voltage data D (1)~D (256) are to be obtained.

When the shading time measurement is completed, the completion of the shading time measurement is displayed on the display panel 36, and the instructions for installing the correcting cover 24 is displayed.

When the operator installs the correcting cover 24 and the position sensor (not shown) detects it, the transmission standard body drive device 20 is automatically actuated to rotate the transmission standard bodies 17, 18, and as shown in FIG. 13, the irradiation light B from the light sources 4, 4 is reflected by the reflecting standard body 26, passes through the transmission light detecting hole 3b, and passes through the transmission standard bodies 17, 18 into the transmission light C, which passes through the optical fiber 28 and is guided to the spectra/detection unit 29, and the standard body measuring state is displayed on the display panel 36.

In the standard body measuring state, the transmission light C is divided into a number of frequency areas by the spectra/detection unit 29, and the optical strength of every frequency area is measured. Here, since the frequency area is divided into 256, the optical strength data R (1)~R (256) are to be obtained.

At the time of the standard body measurement, detection values $P_{w1}$ and $P_{w2}$ of the optical strength having a fixed wavelength are taken into the operation processing unit 31 every fixed period $\tau_1$ (Step 3) to decide whether or not the strength ratio ($P_{w1}/P_{w2}$) of light is smaller than the allowable strength ratio $P_a$ set of light (Step 4).

If the decision is No, the strength ratio ($P_{w1}/P_{w2}$) is not stabilized, and the Steps 3 and 4 are repeated till the decision becomes Yes.

Alternatively, whether or not the strength difference ($P_{w1}-P_{w2}$) is smaller than the allowable strength difference $P_a$ set may be decided, in place of the strength ratio ($P_{w1}/P_{w2}$).

When in Step 4, the decision is Yes, the warming-up operation and the standard body measurement are completed (Step 5), and the measurement preparation completion lamp 35c lights so that the completion of the warming-up operation is displayed on the display panel 36, and the vegetables and fruits measurable state is displayed.

Following operation and effect in the vegetables and fruits measurement are entirely similar to those described above. The quality evaluation amounts such as the sugar degree, the ripening degree, the honey amount, the degree of changing to brown or the like are calculated or decided, and as shown in FIG. 15, are displayed by letters or numerical values together with the kind and the breed of vegetables and fruits on the display panel 36.

According to the warming-up operating method in the apparatus for evaluating the inner quality of vegetables and fruits of the present invention, the apparatus is subjected to warming-up operation only for a period of time as necessary whereby the waiting time which is more than as needed or entirely wasteful is omitted while sufficiently securing the accuracy of measurement and evaluation, and the enhancement of the working efficiency and the energy saving can be realized.

Figure 32:
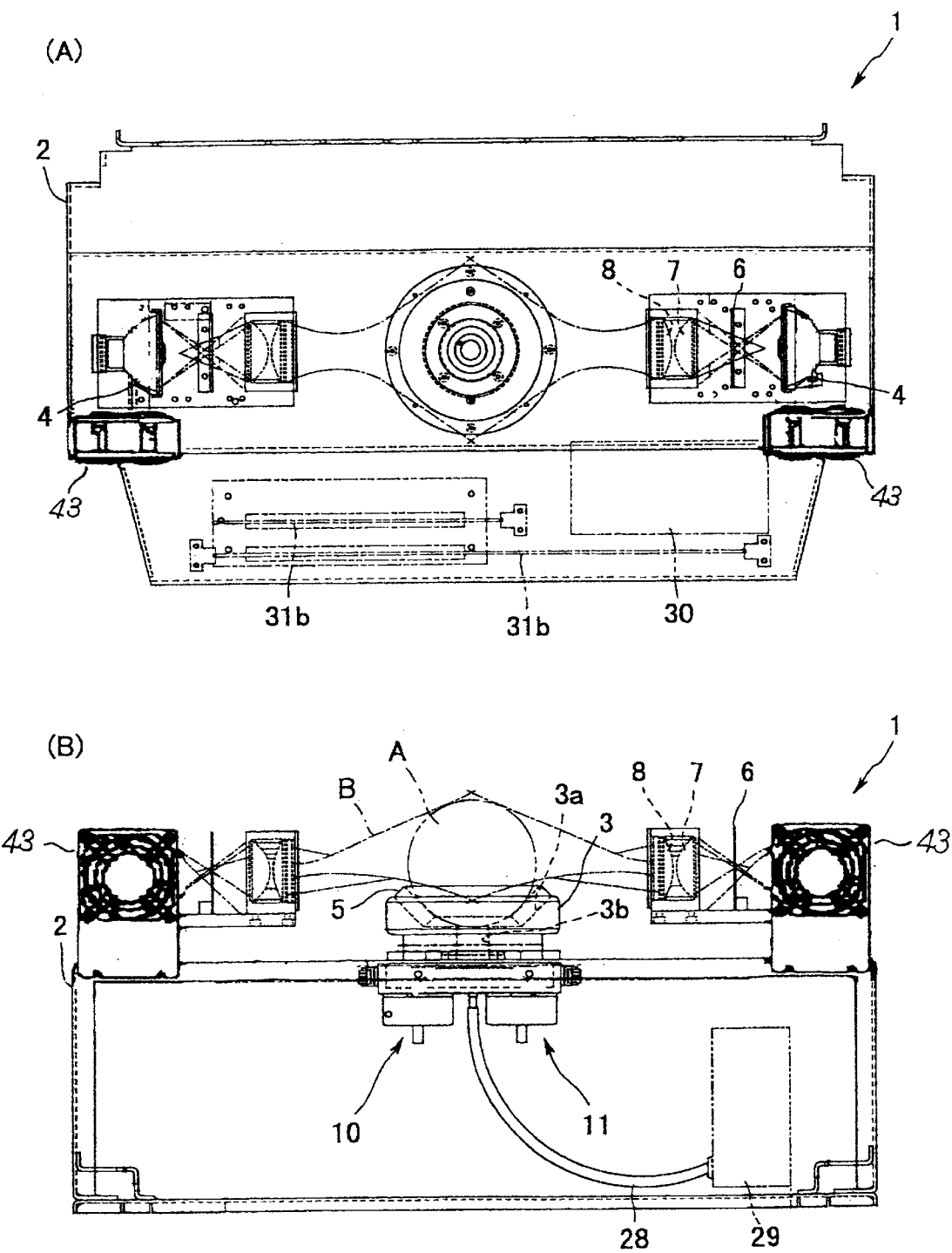
FIGS. 32(A) and 32(B) show the interior of the apparatus for evaluating the inner quality of vegetables and fruits according to another embodiment of the present invention, (A) being a plan view, (B) being a front view.

While normally, light source cooling fans 43, 43 are installed in order to prevent the light sources 4, 4 from being overheated, as shown in FIG. 32, it is noted preferably that the light source cooling fans 43 are not operated till the warming-up operation is completed.

Thereby, the warming-up operating time can be shortened, and further energy saving can be realized.

Further, the light source cooling fans 43 may be operated when the warming-up operation is completed, or after completion of the warming-up operation, the vegetables and fruits A are placed on the place bed, and when the weight sensor or the photo sensor detects it, the fan may be operated. Furthermore, when the measuring button 34 is pressed down, the fan may be operated.

Figure 33:
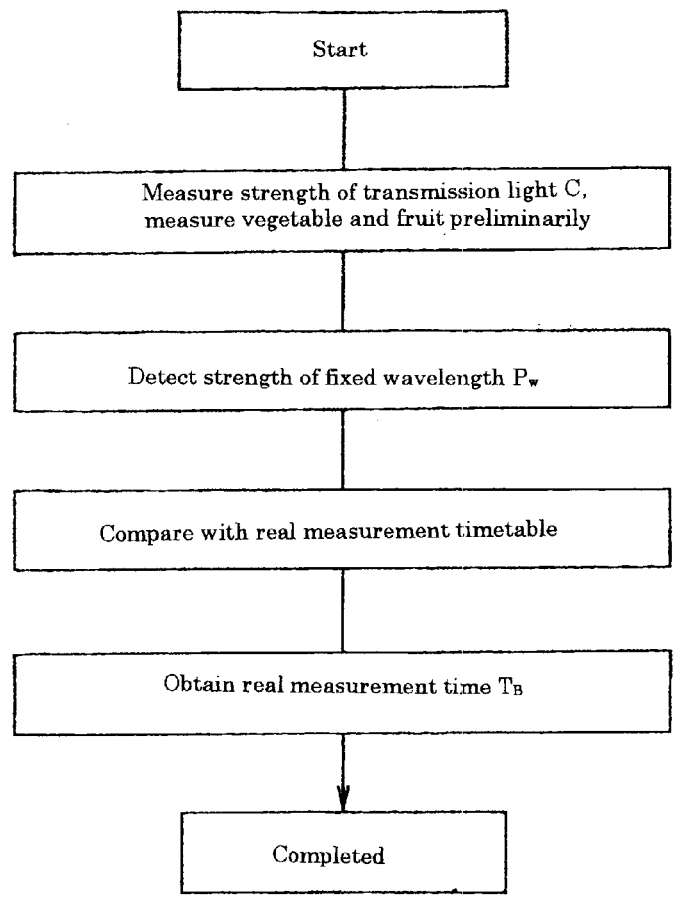
FIG. 33 is a process (step) view showing the inner quality measuring procedure in the apparatus for evaluating the inner quality of vegetables and fruits.

Next, the inner quality measuring method in the apparatus for evaluating the inner quality of vegetables and fruits in which even if there are a variety of kinds and breeds of vegetables and fruits, the inner quality can be measured efficiently while securing the sufficient measuring accuracy, and the constitution of the apparatus can be simplified will be described with reference to FIGS. 11 and 33, together with the operation, function and using method of the apparatus for evaluating the inner quality of vegetables and fruits 1.

The operation and the function till assuming, after the power supply button of the apparatus for evaluating the inner quality of vegetables and fruits 1 is pressed down to turn on the power supply, the warming-up operating state, the shading time measuring state, the standard body measuring state and the vegetables and fruits measuring state, are similar to those described above.

Figure 34:
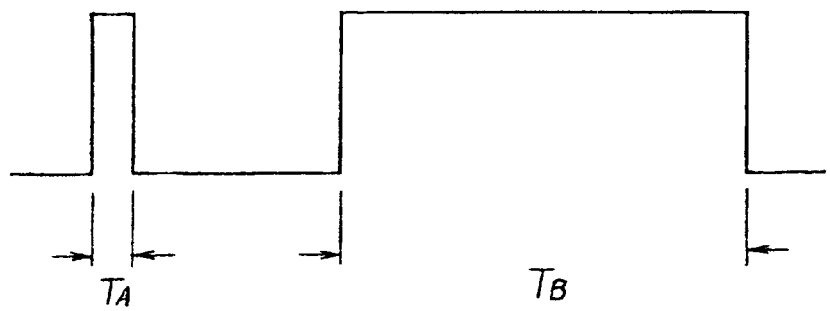
FIG. 34 is an explanatory view showing the measuring time in the preliminary measurement and the real measurement.

In the apparatus 1 to which is applied the inner quality measuring method of the present invention, in the vegetables and fruits measuring state, the strength of the transmission light C is preliminarily measured in a relatively short period of time $T_A$ before the real measurement of the inner quality is executed, as shown in FIG. 34, and the real measuring time $T_B$ of the inner quality is set on the basis of the measured optical strength.

In the present embodiment, the time $T_A$ is about 10 msec, and the measuring time $T_B$ is suitably set within the range of 100 msec~1 sec corresponding to the optical strength.

The transmission light C is divided into a number of frequency areas by the spectra/detection unit 29, and the optical strength of every frequency area is measured. Here, since the frequency area is divided into 256, the optical strength data I (1)~I (256) are obtained.

In the preliminary measurement, the optical strength $P_w$ of a fixed wavelength W is a detection value. As the fixed wavelength W, normally, a wavelength within the range of 700~850 nm indicative of a high value of the optical strength which is most efficient in detection is selected.

On the other hand, a table in which the measuring time T necessary in the real measurement corresponds to the optical strength $P_w$ of a fixed wavelength W detected in the preliminary measurement is stored in a memory (not shown) arranged on PC plates 31a, 31b, as shown in FIG. 35.

In this table, in a case where the optical strength is not more than $P_n$, $T_n$ is set as the measuring time, the measuring time $T_n$ corresponding to the optical strength $P_n$ is experimentally or theoretically obtained.

Since the lower the optical strength $P_n$, the measuring time $T_n$ need be longer, there is established the following relation:

$$T_n < T_{n-1}$$

Further, a functional equation in which the optical strength $P_w$ corresponds to the measuring time T may be provided in place of the table in which the measuring time T corresponds to the optical strength $P_w$.

As described above, when the measuring time $T_B$ is set, the real measurement of the inner quality is then executed, and the strength of the transmission light C is measured in the measuring time $T_B$.

In the present invention, the real measurement of the inner quality is repeated at least five times in order to secure the measuring accuracy, and is executed for 5 sec in total. Thereby, the shorter the measuring time $T_B$, the repeating frequency increases.

The transmission light C is divided into a number of frequency areas by the spectra/detection unit 29, and the optical strength of every frequency area is measured. Here, since the frequency area is divided into 256, the optical strength data S (1)~S (256) are obtained.

When the vegetables and fruits measurement is completed, the absorbance of every frequency area caused by the vegetables and fruits A is calculated as ABS (1)~ABS (256) from the optical strength data S (1)~S (256), R (1)~R (256), and the internally residual voltage data D (1)~D (256) by the operation processing unit 31.

Then, the quality evaluation amounts such as the sugar degree, the ripening degree, the honey amount, the degree of changing to brown or the like are calculated or decided from the absorbance data ABS (1)~ABS (256), and as shown FIG. 15, are displayed by letters or numerical values together with the kind and the breed of vegetables and fruits on the display panel 36.

According to the inner quality measuring method in the apparatus for evaluating the inner quality of vegetables and fruits according to the present invention, the time for measuring the inner quality is set corresponding to the strength of light measured preliminarily, and the real inner quality is measured in the thus set time. Therefore, even if the kind and the breed of vegetables and fruits are varied, the inner quality can be measured efficiently while securing the sufficient measuring accuracy.

Further, according to the inner quality measuring method in the apparatus for evaluating the inner quality of vegetables and fruits of the present invention, since an amplifier having a multistage gain is not necessary, the constitution of the apparatus for evaluating the inner quality of vegetables and fruits can be also simplified.

What is claimed is:

1. An apparatus for evaluating the inner quality of vegetables and fruits comprising:
    a place bed formed with a conical shape defined by curved before surfaces and having at one end thereof a rim for receiving vegetables and fruits and at an opposite apex end thereof a transmission light detecting hole over which vegetables and fruits are placed;
    light sources disposed opposedly on both sides of the place bed and above said rim to irradiate vegetables and fruits;
    a spectra/detection unit for making spectra in transmission light having transmitted through vegetables and fruits and passed through the transmission light detecting hole and detecting optical strength;
    an A/D converter for converting an analogue detection signal into a digital detection signal;
    an operation processing section for calculating and evaluating the quality evaluation amount of the sugar degree and the ripening degree on the basis of the detection signals;
    a measuring button for instructing the measurement; and
    a display panel for displaying the quality evaluation amount of the sugar degree and the ripening degree, the apparatus capable of being installed on the table, and also being portable.

2. An apparatus for evaluating the inner quality of vegetables and fruits comprising:
    a place bed formed with a conical shape defined by curved before surfaces and having at one end thereof a rim for receiving vegetables and fruits and at an opposite apex end thereof a transmission light detecting hole over which vegetables and fruits are placed;
    light sources disposed opposedly on both sides of the place bed and above said rim to irradiate vegetables and fruits;
    a spectra/detection unit for making spectra in transmission light having transmitted through vegetables and fruits and passed through the transmission light detecting hole and detecting optical strength;
    an A/D converter for converting an analogue detection signal into a digital detection signal;
    an operation processing section for calculating and evaluating the quality evaluation amount of the sugar degree and the ripening degree on the basis of the detection signals;
    a display panel for displaying the quality evaluation amount of the sugar degree and the ripening degree; and
    detection means for detecting whether or not vegetables and fruits are placed on the place bed, the apparatus capable of being installed on the table, and also being portable,
    wherein when the detection means detects that vegetables and fruits are placed on the place bed, the measurement is automatically started.

3. The apparatus for evaluating the inner quality of vegetables and fruits according to claim 2, wherein said detection means comprises a position sensor.

4. The apparatus for evaluating the inner quality of vegetables and fruits according to claim 2, wherein said detection means preliminarily measures the strength of the transmission light to compare it with the detected optical strength.

5. The apparatus for evaluating the inner quality of vegetables and fruits according to claims 1 or 2, wherein said transmission light detecting hole and said spectra/detection unit are connected by an optical fiber.

6. The apparatus for evaluating the inner quality of vegetables and fruits according to claims 1 or 2, wherein said place bed planar surfaces comprise a fitting depressed portion on which vegetables and fruits are placed, and the fitting depressed portion is formed with a transmission light detecting hole extending to the bottom.

7. The apparatus for evaluating the inner quality of vegetables and fruits according to claims 1 or 2, wherein said place bed is that a holding material comprising a sponge is installed on the fitting depressed portion.

8. The apparatus for evaluating the inner quality of vegetables and fruits according to claims 1 or 2, wherein said spectra/detection unit is that the transmission light having transmitted through vegetables and fruits is divided into a number of frequency areas to detect the optical strength of each frequency area.

9. The apparatus for evaluating the inner quality of vegetables and fruits according to claims 1 or 2, wherein a shutter opening and closing device comprising a shutter for shielding light having passed through said transmission light detecting hole and a shutter driving device for moving the shutter is disposed.

10. The apparatus for evaluating the inner quality of vegetables and fruits according to claims 1 or 2, wherein a transmission standard body setting device comprising a transmission standard body for transmitting light having passed through said transmission light detecting hole and a transmission standard body driving device for moving the transmission standard body is disposed.

11. The apparatus for evaluating the inner quality of vegetables and fruits according to claims 1 or 2, wherein a peripheral temperature of a light source is detected in a manner of a lapse of time, the peripheral temperature of a light source is compared with a safety setting temperature, and the fact that the light source temperature is completely lowered is reported.

12. The apparatus for evaluating the inner quality of vegetables and fruits according to claim 11, wherein an environment temperature is detected in a manner of a lapse of time, and the peripheral temperature of a light source is also compared with the environment temperature whereby the fact that the light source temperature is completely lowered is reported.

13. An apparatus for evaluating the inner quality of vegetables and fruits comprising:
   a place bed formed with a transmission light detecting hole and on which vegetables and fruits are placed;
   light sources disposed opposedly on both sides of the place bed and above said rim to irradiate vegetables and fruits;
   a spectra/detection unit for making spectra in transmission light having transmitted through vegetables and fruits and passed through the transmission light detecting hole and detecting optical strength;
   an A/D converter for converting an analogue detection signal into a digital detection signal;
   an operation processing section for calculating and evaluating the quality evaluation amount of the sugar degree and the ripening degree on the basis of the detection signals;
   a display panel for displaying the quality evaluation amount of the sugar degree and the ripening degree; and
   detection means for detecting whether or not vegetables and fruits are placed on the place bed, the apparatus capable of being installed on the table, and also being portable,
   wherein when the detection means detects that vegetables and fruits are placed on the place bed, the measurement is automatically started,
   wherein said detection means comprises a weight sensor.

14. A warming-up operating method in an apparatus for evaluating the inner quality of vegetables and fruits comprising: automatically judging that a spectra of a light source is stabilized to decide the termination of the warming-up operation, and executing the warming-up operation till the termination of the warming-up operation, wherein a spectra of a light source is detected in a manner of a lapse of time, whether or not the spectra of the light source is stabilized by the strength ratio of light having a fixed wavelength or the strength difference is judged, and the completion time of the warming up-operation is decided.

15. The warming-up operating method in apparatus for evaluating the inner quality of vegetables and fruits according to claim 14, wherein a peripheral temperature of a light source is detected in a manner of a lapse of time, whether or not the spectra of the light source is stabilized is judged on the basis of stabilization of the peripheral temperature, and the completion time of the warming up operation is decided.

16. A warming-up operating method in an apparatus for evaluating the inner quality of vegetables and fruits comprising: automatically judging that a spectra of a light source is stabilized to decide the termination of the warming-up operation, and executing the warming-up operation till the termination of the warming-up operation,
   wherein a peripheral temperature of a light source is detected in a manner of a lapse of time, whether or not the spectra of the light source is stabilized is judged on the basis of stabilization of the peripheral temperature, and the completion time of the warming-up operation is decided, and
   wherein a fixed time ts is added after the stabilization of the peripheral temperature to thereby decide the completion time of the warming-up operation.

17. The warming-up operating method in an apparatus for evaluating the inner quality of vegetables and fruits according to claim 16, wherein confirmation is made of that the strength of light having a fixed wavelength be within the allowable range to decide the completion of the warming-up operation.

18. The warming-up operating method in an apparatus for evaluating the inner quality of vegetables and fruits according to any one of claims 14, 15, 16 or 17, comprising executing the warming-up operation without operating a light source cooling fan till the completion of the warming-up operation, and operating the light source cooling fan after the completion of the warming-up operation.

19. A method for measuring the inner quality in an apparatus for evaluating the inner quality of vegetables and fruits, comprising preliminarily measuring the strength of light having reflected or transmitted through vegetables and fruits in a relatively short period of time before the inner quality of vegetables and fruits is measured really, setting the time for measuring the inner quality corresponding to the strength of light measured, measuring the strength of light having reflected or transmitted through vegetables and fruits in the measuring time set, and measuring the inner quality really.

20. The method for measuring the inner quality in an apparatus for evaluating the inner quality of vegetables and fruits according to claim 19, wherein a table in which the measuring time necessary in the real measurement corresponds to the strength of light measured in the preliminary measurement is set, the measured value of the strength of light is collated to the table, and the measuring time necessary in the real measurement is set.

21. The method for measuring the inner quality in an apparatus for evaluating the inner quality of vegetables and fruits according to claim 19 or 20, wherein as the strength of light in the preliminary measurement, the strength of light having a fixed wavelength is employed.

22. The method for measuring the inner quality in an apparatus for evaluating the inner quality of vegetables and fruits according to claim 21, wherein as the fixed wavelength, a wavelength within the range of 700~850 nm is employed.

* * * * *